US009670215B2

(12) United States Patent
Ahmad et al.

(10) Patent No.: US 9,670,215 B2
(45) Date of Patent: Jun. 6, 2017

(54) COMPOUNDS USEFUL AS INHIBITORS OF ATR KINASE

(71) Applicant: Vertex Pharmaceuticals Incorporated, Boston, MA (US)

(72) Inventors: Nadia Ahmad, Didcot (GB); Jean-Damien Charrier, Wantage (GB); Chris Davis, Salisbury (GB); Gorka Etxebarria I Jardi, Abingdon (GB); Damien Fraysse, Abingdon (GB); Ronald Knegtel, Abingdon (GB); Maninder Panesar, Didcot (GB); Francoise Pierard, Abingdon (GB); Joanne Pinder, Didcot (GB); Pierre-Henri Storck, Abingdon (GB); John Studley, Witney (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 14/723,599

(22) Filed: May 28, 2015

(65) Prior Publication Data
US 2015/0353560 A1 Dec. 10, 2015

Related U.S. Application Data

(60) Provisional application No. 62/008,277, filed on Jun. 5, 2014.

(51) Int. Cl.
C07D 487/04 (2006.01)
(52) U.S. Cl.
CPC .................. C07D 487/04 (2013.01)
(58) Field of Classification Search
CPC .................................................. C07D 487/04
See application file for complete search history.

(56) References Cited

U.S. PATENT DOCUMENTS

| | | | |
|---|---|---|---|
| 4,309,430 A | 1/1982 | Bock et al. | |
| 5,143,824 A | 9/1992 | Yamakawa et al. | |
| 6,060,478 A | 5/2000 | Gilligan et al. | |
| 6,191,131 B1 | 2/2001 | He et al. | |
| 6,235,741 B1 | 5/2001 | Bilodeau et al. | |
| 6,660,753 B2 | 12/2003 | Van Wagenen et al. | |
| 6,858,600 B2 | 2/2005 | Hamilton et al. | |
| 6,992,087 B2 | 1/2006 | Verhoest et al. | |
| 7,041,672 B2 | 5/2006 | Verhoest et al. | |
| 7,199,123 B2 | 4/2007 | Munchhof | |
| 7,452,993 B2 | 11/2008 | Arnold et al. | |
| 7,528,138 B2 | 5/2009 | Knegtel et al. | |
| 7,550,470 B2 | 6/2009 | Fraley | |
| 7,622,583 B2 | 11/2009 | Ungashe et al. | |
| 7,626,021 B2 | 12/2009 | Arnold et al. | |
| 7,700,601 B2 | 4/2010 | Chan et al. | |
| 7,704,995 B2 | 4/2010 | Buhr et al. | |
| 7,829,558 B2 | 11/2010 | Arnold et al. | |
| 7,872,031 B2 | 1/2011 | Lauffer et al. | |
| 7,902,197 B2 | 3/2011 | Elworthy et al. | |

(Continued)

FOREIGN PATENT DOCUMENTS

| | | |
|---|---|---|
| CN | 101537007 A | 9/2009 |
| CN | 101671336 A | 3/2010 |

(Continued)

OTHER PUBLICATIONS

Chawla et al., 2004, CRIPS vol. 5 No. 1. 9-12.*
International Search Report for PCT/US2005/040344 mailed Mar. 20, 2006.
International Search Report and Written Opinion dated Sep. 24, 2015 in connection with Application No. PCT/US2015/036137.
International Search Report and Written Opinion dated Feb. 6, 2014 in connection with Application No. PCT/US2013/073482.
International Search Report and Written Opinion in connection with Application No. PCT/US2012/043897 mailed Jul. 20, 2012.
International Search Report and Written Opinion in connection with Application No. PCT/US2012/043896 mailed Oct. 9, 2012.

(Continued)

*Primary Examiner* — Sun Jae Yoo
(74) *Attorney, Agent, or Firm* — Andrea L. C. Reid; Dechert LLP

(57) ABSTRACT

The present invention relates to compounds useful as inhibitors of ATR protein kinase. The invention relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and solid forms of the compounds of this invention.
The compounds of this invention have formula I-1 or I-A:

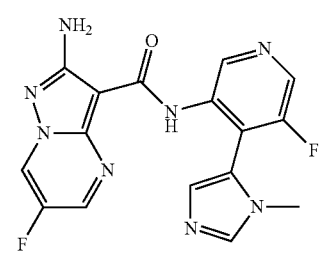

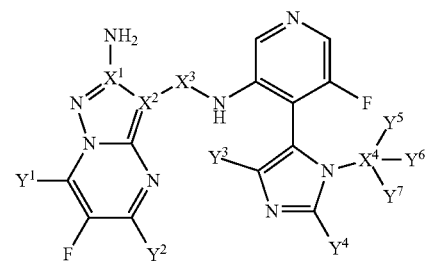

wherein the variables are as defined herein.

3 Claims, 5 Drawing Sheets

(56) References Cited

U.S. PATENT DOCUMENTS

| | | | |
|---|---|---|---|
| 7,932,254 B2 | 4/2011 | DuBois et al. | |
| 7,939,531 B2 | 5/2011 | Bamberg et al. | |
| 7,981,893 B2 | 7/2011 | Mortensen et al. | |
| 8,063,032 B2 | 11/2011 | Chytil et al. | |
| 8,106,197 B2 | 1/2012 | Cui et al. | |
| 8,410,112 B2 | 4/2013 | Charrier et al. | |
| 8,492,582 B2 | 7/2013 | Yokotani et al. | |
| 8,623,869 B2 | 1/2014 | Charrier et al. | |
| 8,822,469 B2 | 9/2014 | MacCormick et al. | |
| 8,957,078 B2 | 2/2015 | Brenchley et al. | |
| 8,962,631 B2 | 2/2015 | Charrier et al. | |
| 8,969,360 B2 | 3/2015 | Charrier et al. | |
| 9,096,602 B2 | 8/2015 | Everitt et al. | |
| 9,309,250 B2 | 4/2016 | Storck et al. | |
| 9,340,546 B2 * | 5/2016 | Ahmad | C07D 487/04 |
| 2002/0041880 A1 | 4/2002 | DeFeo-Jones et al. | |
| 2003/0008882 A1 | 1/2003 | Hamilton et al. | |
| 2003/0055085 A1 | 3/2003 | Wagenen et al. | |
| 2004/0034037 A1 | 2/2004 | Harbeson et al. | |
| 2004/0180905 A1 | 9/2004 | Munchhof | |
| 2006/0156482 A1 | 7/2006 | Lim | |
| 2006/0211709 A1 | 9/2006 | Buhr et al. | |
| 2007/0037794 A1 | 2/2007 | Ungashe et al. | |
| 2007/0254868 A1 | 11/2007 | Lauffer et al. | |
| 2007/0270420 A1 | 11/2007 | Harbeson et al. | |
| 2007/0287711 A1 | 12/2007 | Arnold et al. | |
| 2009/0005381 A1 | 1/2009 | Brown et al. | |
| 2009/0215724 A1 | 8/2009 | DuBois et al. | |
| 2009/0215750 A1 | 8/2009 | Bamberg et al. | |
| 2009/0215785 A1 | 8/2009 | DuBois et al. | |
| 2009/0215788 A1 | 8/2009 | Elworthy et al. | |
| 2009/0306087 A1 | 12/2009 | Ibrahim et al. | |
| 2009/0318436 A1 | 12/2009 | Albrecht et al. | |
| 2010/0036118 A1 | 2/2010 | Arnold et al. | |
| 2010/0168138 A1 | 7/2010 | DeGoey et al. | |
| 2010/0204214 A1 | 8/2010 | Chytil et al. | |
| 2010/0222318 A1 | 9/2010 | Charrier et al. | |
| 2010/0233091 A1 | 9/2010 | Neumann et al. | |
| 2011/0015231 A1 | 1/2011 | Al-Abed et al. | |
| 2011/0275797 A1 | 11/2011 | Yokotani et al. | |
| 2011/0288067 A1 | 11/2011 | Hendricks et al. | |
| 2011/0288097 A1 | 11/2011 | Hendricks et al. | |
| 2012/0027874 A1 | 2/2012 | Charrier et al. | |
| 2012/0035407 A1 | 2/2012 | Charrier et al. | |
| 2012/0035408 A1 | 2/2012 | Charrier et al. | |
| 2012/0040020 A1 | 2/2012 | Charrier et al. | |
| 2012/0046295 A1 | 2/2012 | Charrier et al. | |
| 2012/0065247 A1 | 3/2012 | Thompson et al. | |
| 2012/0115874 A1 | 5/2012 | Wang et al. | |
| 2012/0122884 A1 | 5/2012 | Charrier et al. | |
| 2012/0177748 A1 | 7/2012 | Charrier et al. | |
| 2012/0178756 A1 | 7/2012 | Charrier et al. | |
| 2013/0017273 A1 | 1/2013 | Everitt et al. | |
| 2013/0018035 A1 | 1/2013 | MacCormick et al. | |
| 2013/0034616 A1 | 2/2013 | Storck et al. | |
| 2013/0089624 A1 | 4/2013 | Charrier et al. | |
| 2013/0089625 A1 | 4/2013 | Charrier et al. | |
| 2013/0089626 A1 | 4/2013 | Pollard et al. | |
| 2013/0095193 A1 | 4/2013 | Charrier et al. | |
| 2013/0096139 A1 | 4/2013 | Charrier et al. | |
| 2013/0115310 A1 | 5/2013 | Charrier et al. | |
| 2013/0115311 A1 | 5/2013 | Charrier et al. | |
| 2013/0115312 A1 | 5/2013 | Charrier et al. | |
| 2013/0115313 A1 | 5/2013 | Charrier et al. | |
| 2013/0115314 A1 | 5/2013 | Charrier et al. | |
| 2013/0172273 A1 | 7/2013 | Aizpurua Iparraguirre et al. | |
| 2013/0184292 A1 | 7/2013 | Charrier et al. | |
| 2014/0113005 A1 | 4/2014 | Charrier et al. | |
| 2014/0163000 A1 | 6/2014 | Ahmad et al. | |
| 2014/0249157 A1 | 9/2014 | Ahmad et al. | |
| 2014/0275009 A1 | 9/2014 | Brenchley et al. | |
| 2014/0275021 A1 | 9/2014 | Charrier et al. | |
| 2014/0275130 A1 | 9/2014 | Charrier et al. | |
| 2014/0288347 A1 | 9/2014 | Charrier et al. | |
| 2015/0158868 A1 | 6/2015 | Boyall et al. | |
| 2015/0158872 A1 | 6/2015 | Charrier et al. | |
| 2015/0291601 A1 | 10/2015 | Brenchley et al. | |
| 2015/0299205 A1 | 10/2015 | Charrier et al. | |
| 2015/0359797 A1 | 12/2015 | Helleday et al. | |
| 2015/0376187 A1 | 12/2015 | Everitt et al. | |
| 2016/0009723 A1 | 1/2016 | Charrier et al. | |

FOREIGN PATENT DOCUMENTS

| | | |
|---|---|---|
| CN | 103373996 A | 10/2013 |
| EP | 0313724 A2 | 5/1989 |
| EP | 1217000 A1 | 6/2002 |
| EP | 2157090 A1 | 2/2010 |
| JP | 2001-302666 A | 10/2001 |
| WO | WO 96/35690 A1 | 11/1996 |
| WO | WO 97/43267 A1 | 11/1997 |
| WO | WO 98/03510 A1 | 1/1998 |
| WO | WO 98/33799 A1 | 8/1998 |
| WO | WO 98/42701 A1 | 10/1998 |
| WO | WO 98/54093 A1 | 12/1998 |
| WO | WO 00/04014 A1 | 1/2000 |
| WO | WO 00/53605 A1 | 9/2000 |
| WO | WO 01/40231 A1 | 6/2001 |
| WO | WO 01/44206 A1 | 6/2001 |
| WO | WO 01/92257 A1 | 12/2001 |
| WO | WO 02/09648 A2 | 2/2002 |
| WO | WO 02/40485 A1 | 5/2002 |
| WO | WO 02/066481 A1 | 8/2002 |
| WO | WO 03/000187 A2 | 1/2003 |
| WO | WO 03/004472 A1 | 1/2003 |
| WO | WO 03/004475 A1 | 1/2003 |
| WO | WO 03/037900 A2 | 5/2003 |
| WO | WO 03/045924 A1 | 6/2003 |
| WO | WO 03/076422 A1 | 9/2003 |
| WO | WO 03/080610 A1 | 10/2003 |
| WO | WO 03/087057 A1 | 10/2003 |
| WO | WO 03/092686 A1 | 11/2003 |
| WO | WO 03/093297 A2 | 11/2003 |
| WO | WO 03/101968 A1 | 12/2003 |
| WO | WO 03/101993 A1 | 12/2003 |
| WO | WO 04/000318 A2 | 12/2003 |
| WO | WO 2004/022559 A1 | 3/2004 |
| WO | WO 2004/022560 A1 | 3/2004 |
| WO | WO 2004/022561 A1 | 3/2004 |
| WO | WO 2004/026229 A2 | 4/2004 |
| WO | WO 2004/033431 A2 | 4/2004 |
| WO | WO 2004/052315 A2 | 6/2004 |
| WO | WO 2004/055005 A1 | 7/2004 |
| WO | WO 2004/055006 A1 | 7/2004 |
| WO | WO 2004/076458 A1 | 9/2004 |
| WO | WO 2004/080982 A1 | 9/2004 |
| WO | WO 2004/084813 A2 | 10/2004 |
| WO | WO 2004/084824 A2 | 10/2004 |
| WO | WO 2004/085409 A2 | 10/2004 |
| WO | WO 2004/103279 A2 | 12/2004 |
| WO | WO 2005/028434 A2 | 3/2005 |
| WO | WO 2005/028475 A2 | 3/2005 |
| WO | WO 2005/051906 A2 | 6/2005 |
| WO | WO 2005/054246 A2 | 6/2005 |
| WO | WO 2005/077954 A2 | 8/2005 |
| WO | WO 2005/079802 A1 | 9/2005 |
| WO | WO 2005/080396 A2 | 9/2005 |
| WO | WO 2005/117909 A2 | 12/2005 |
| WO | WO 2005/123672 A2 | 12/2005 |
| WO | WO 2006/015124 A2 | 2/2006 |
| WO | WO 2006/052913 A1 | 5/2006 |
| WO | WO 2006/053342 A2 | 5/2006 |
| WO | WO 2006/058074 A1 | 6/2006 |
| WO | WO 2006/067462 A1 | 6/2006 |
| WO | WO 2006/071548 A2 | 7/2006 |
| WO | WO 2006/071752 A1 | 7/2006 |
| WO | WO 2006/075152 A1 | 7/2006 |
| WO | WO 2006/087120 A2 | 8/2006 |
| WO | WO 2006/088837 A2 | 8/2006 |
| WO | WO 2006/114180 A1 | 11/2006 |
| WO | WO 2006/120573 A2 | 11/2006 |
| WO | WO 2006/128184 A2 | 11/2006 |
| WO | WO 2007/015632 A1 | 2/2007 |
| WO | WO 2007/041712 A1 | 4/2007 |

(56) References Cited

FOREIGN PATENT DOCUMENTS

| | | |
|---|---|---|
| WO | WO 2007/044401 A2 | 4/2007 |
| WO | WO 2007/044407 A2 | 4/2007 |
| WO | WO 2007/044410 A1 | 4/2007 |
| WO | WO 2007/044420 A1 | 4/2007 |
| WO | WO 2007/044426 A2 | 4/2007 |
| WO | WO 2007/044441 A2 | 4/2007 |
| WO | WO 2007/044449 A2 | 4/2007 |
| WO | WO 2007/046548 A1 | 4/2007 |
| WO | WO 2007/048066 A2 | 4/2007 |
| WO | WO 2007/058850 A2 | 5/2007 |
| WO | WO 2007/063012 A1 | 6/2007 |
| WO | WO 2007/066805 A1 | 6/2007 |
| WO | WO 2007/076360 A1 | 7/2007 |
| WO | WO 2007/096151 A2 | 8/2007 |
| WO | WO 2007/096764 A2 | 8/2007 |
| WO | WO 2007/096765 A1 | 8/2007 |
| WO | WO 2007/102770 A1 | 9/2007 |
| WO | WO 2007/111904 A2 | 10/2007 |
| WO | WO 2007/126841 A2 | 11/2007 |
| WO | WO 2007/126964 A2 | 11/2007 |
| WO | WO 2007/139732 A1 | 12/2007 |
| WO | WO 2007/139856 A2 | 12/2007 |
| WO | WO 2007/139860 A2 | 12/2007 |
| WO | WO 2007/147874 A1 | 12/2007 |
| WO | WO 2008/004698 A2 | 1/2008 |
| WO | WO 2008/008539 A2 | 1/2008 |
| WO | WO 2008/037477 A1 | 4/2008 |
| WO | WO 2008/038010 A1 | 4/2008 |
| WO | WO 2008/040651 A1 | 4/2008 |
| WO | WO 2008/045266 A2 | 4/2008 |
| WO | WO 2008/045268 A2 | 4/2008 |
| WO | WO 2008/060907 A2 | 5/2008 |
| WO | WO 2008/063671 A2 | 5/2008 |
| WO | WO 2008/071456 A2 | 6/2008 |
| WO | WO 2008/074997 A1 | 6/2008 |
| WO | WO 2008/079291 A2 | 7/2008 |
| WO | WO 2008/079903 A1 | 7/2008 |
| WO | WO 2008/079906 A1 | 7/2008 |
| WO | WO 2008/103277 A2 | 8/2008 |
| WO | WO 2008/106692 A1 | 9/2008 |
| WO | WO 2008/122375 A2 | 10/2008 |
| WO | WO 2008/124850 A1 | 10/2008 |
| WO | WO 2008/130569 A1 | 10/2008 |
| WO | WO 2008/130570 A1 | 10/2008 |
| WO | WO 2008/141065 A1 | 11/2008 |
| WO | WO 2008/144463 A1 | 11/2008 |
| WO | WO 2008/144464 A1 | 11/2008 |
| WO | WO 2008/151735 A2 | 12/2008 |
| WO | WO 2008/157191 A2 | 12/2008 |
| WO | WO 2009/006580 A1 | 1/2009 |
| WO | WO 2009/007390 A2 | 1/2009 |
| WO | WO 2009/012482 A2 | 1/2009 |
| WO | WO 2009/014637 A2 | 1/2009 |
| WO | WO 2009/016460 A2 | 2/2009 |
| WO | WO 2009/017954 A1 | 2/2009 |
| WO | WO 2009/024825 A1 | 2/2009 |
| WO | WO 2009/037247 A1 | 3/2009 |
| WO | WO 2009/053737 A2 | 4/2009 |
| WO | WO 2009/070567 A1 | 6/2009 |
| WO | WO 2009/075790 A1 | 6/2009 |
| WO | WO 2009/088986 A1 | 7/2009 |
| WO | WO 2009/091374 A2 | 7/2009 |
| WO | WO 2009/095254 A1 | 8/2009 |
| WO | WO 2009/106885 A1 | 9/2009 |
| WO | WO 2009/117157 A1 | 9/2009 |
| WO | WO 2010/002483 A1 | 1/2010 |
| WO | WO 2010/006086 A2 | 1/2010 |
| WO | WO 2010/015803 A1 | 2/2010 |
| WO | WO 2010/017047 A1 | 2/2010 |
| WO | WO 2010/034738 A2 | 4/2010 |
| WO | WO 2010/048131 A1 | 4/2010 |
| WO | WO 2010/051549 A1 | 5/2010 |
| WO | WO 2010/054398 A1 | 5/2010 |
| WO | WO 2010/059836 A1 | 5/2010 |
| WO | WO 2010/063634 A1 | 6/2010 |
| WO | WO 2010/068483 A2 | 6/2010 |
| WO | WO 2010/071837 A1 | 6/2010 |
| WO | WO 2010/086040 A1 | 8/2010 |
| WO | WO 2010/091409 A1 | 8/2010 |
| WO | WO 2011/003065 A2 | 1/2011 |
| WO | WO 2011/008830 A1 | 1/2011 |
| WO | WO 2011/022439 A1 | 2/2011 |
| WO | WO 2011/025706 A2 | 3/2011 |
| WO | WO 2011/068667 A1 | 6/2011 |
| WO | WO 2011/113606 A1 | 9/2011 |
| WO | WO 2011/117145 A2 | 9/2011 |
| WO | WO 2011/121096 A1 | 10/2011 |
| WO | WO 2011/124998 A1 | 10/2011 |
| WO | WO 2011/130689 A1 | 10/2011 |
| WO | WO 2011/143399 A1 | 11/2011 |
| WO | WO 2011/143419 A1 | 11/2011 |
| WO | WO 2011/143422 A1 | 11/2011 |
| WO | WO 2011/143423 A2 | 11/2011 |
| WO | WO 2011/143425 A2 | 11/2011 |
| WO | WO 2011/143426 A1 | 11/2011 |
| WO | WO 2011/144584 A1 | 11/2011 |
| WO | WO 2011/144585 A1 | 11/2011 |
| WO | WO 2011/163518 A1 | 12/2011 |
| WO | WO 2012/007375 A1 | 1/2012 |
| WO | WO 2012/022045 A1 | 2/2012 |
| WO | WO 2012/027236 A1 | 3/2012 |
| WO | WO 2012/067822 A1 | 5/2012 |
| WO | WO 2012/074754 A1 | 6/2012 |
| WO | WO 2012/078855 A1 | 6/2012 |
| WO | WO 2012/100342 A1 | 8/2012 |
| WO | WO 2012/138938 A1 | 10/2012 |
| WO | WO 2012/143510 A1 | 10/2012 |
| WO | WO 2012/143796 A2 | 10/2012 |
| WO | WO 2012/158785 A1 | 11/2012 |
| WO | WO 2012/177997 A1 | 12/2012 |
| WO | WO 2012/178124 A1 | 12/2012 |
| WO | WO 2013/010136 A2 | 1/2013 |
| WO | WO 2013/049720 A1 | 4/2013 |
| WO | WO 2013/049726 A2 | 4/2013 |
| WO | WO 2013/052263 A2 | 4/2013 |
| WO | WO 2013/059587 A1 | 4/2013 |
| WO | WO 2013/138436 A1 | 9/2013 |
| WO | WO 2013/151930 A1 | 10/2013 |
| WO | WO 2013/151938 A1 | 10/2013 |
| WO | WO 2013/154878 A1 | 10/2013 |
| WO | WO 2013/171470 A1 | 11/2013 |
| WO | WO 2013/174930 A2 | 11/2013 |
| WO | WO 2013/174931 A1 | 11/2013 |
| WO | WO 2014/011911 A2 | 1/2014 |
| WO | WO 2014/015523 A1 | 1/2014 |
| WO | WO 2014/023691 A1 | 2/2014 |
| WO | WO 2014/025850 A1 | 2/2014 |
| WO | WO 2014/025852 A1 | 2/2014 |
| WO | WO 2014/025854 A1 | 2/2014 |
| WO | WO 2014/026984 A1 | 2/2014 |
| WO | WO 2014/029723 A1 | 2/2014 |
| WO | WO 2014/035140 A2 | 3/2014 |
| WO | WO 2014/039831 A1 | 3/2014 |
| WO | WO 2014/042433 A2 | 3/2014 |
| WO | WO 2014/044691 A1 | 3/2014 |
| WO | WO 2014/047648 A1 | 3/2014 |
| WO | WO 2014/066435 A1 | 5/2014 |
| WO | WO 2014/066552 A1 | 5/2014 |
| WO | WO 2014/089379 A1 | 6/2014 |

OTHER PUBLICATIONS

International Search Report and Written Opinion in connection with Application No. PCT/US2012/043895 mailed Aug. 28, 2012.
International Search Report and Written Opinion dated Oct. 1, 2014 in connection with Application No. PCT/US2015/032879.
International Search Report and Written Opinion dated Jan. 29, 2014 in connection with Application No. PCT/US2013/073457.
International Search Report and Written Opinion mailed Jan. 30, 2014 in connection with Application No. PCT/US2013/073477.
International Search Report and Written Opinion mailed Feb. 17, 2014 in connection with Application No. PCT/US2013/073471.

(56) References Cited

OTHER PUBLICATIONS

International Search Report and Written Opinion dated Jan. 29, 2015 in connection with Application No. PCT/US2014/068713.
International Search Report and Written Opinion dated Apr. 1, 2014 in connection with Application No. PCT/US2013/073468.
International Search Report and Written Opinion in connection with Application No. PCT/US2011/041705 mailed Aug. 23, 2011.
Abdel-Magid, Inhibitors of ATR Kinase for Treatment of Cancer. ACS Med Chem Lett. Jun. 13, 2013;4(8):688-9. doi: 10.1021/ml4002198. eCollection 2013.
Ahmed et al., Synthesis and anti-tumor activities of some new pyridines and pyrazolo[1,5-a]pyrimidines. Eur J Med Chem. Sep. 2009;44(9):3519-23. doi: 10.1016/j.ejmech.2009.03.042. Epub Apr. 8, 2009.
Ahmed et al., Synthesis of some Pyrazolopyrimidines as Purine Analogues. J Heterocyclic Chem. 2007;44(4):803-10.
Ammar et al., 3-Ethoxycarbonylmethylenequinoxalin-2-one in heterocyclic synthesis. Part 1: Synthesis of new substituted and condensed quinoxalines. Afinidad. 2005;62(516):151-60.
Boylan et al., Parenteral Products. Chapter 12. In: Modern Pharmaceuticals. Fourth Edition. 1997:34 pages.
Charrier et al, Discovery of potent and selective inhibitors of ataxia telangiectasia mutated and Rad3 related (ATR) protein kinase as potential anticancer agents. J Med Chem. Apr. 14, 2011;54(7):2320-30. doi: 10.1021/jm101488z. Epub Mar. 17, 2011. E-pub version.
Charrier et al., Discovery of Potent and Selective Inhibitors of ATR (Ataxia Telangiectasia Mutated and Rad3 Related) as Potential AntiCancer Agents. Supplementary Information, Apr. 14, 2011: 47 pages.
Charrier, Discovery of potent and selective inhibitors of Ataxia Telangiectasia mutated and Rad3 related (ATR) protein kinase as potential anticancer agents. Presentation, ACS Denver 2011. Aug. 28, 2011. 21 pages.
Clark et al., Mass spectrometry of pyrrolo [2, 3- b] pyrazines and pyrazino [2, 3- b]indole. Organic Mass Spectrometry. 1977;12(7):421-3.
Curtin, Inhibiting the DNA damage response as a therapeutic manoeuvre in cancer. Br J Pharmacol. Aug. 2013;169(8):1745-65. doi: 10.1111/bph.12244.
El-Emary, Synthesis and Biological Activity of Some New Pyrazolo[3,4-b]pyrazines. J Chinese Chem Soc (Taipei, Taiwan). 2006;53(2): 391-401.
Elnagdi et al., Synthesis of Substituted Azaindenes: Synthesis of New Pyrazolo[1,5-a]pyrimidine Derivatives . Bull Chem Soc Jpn. 1990;63(6):1854-56.
Fernandes et al., Synthesis and Biological Activity of Heterocyclic Derivatives derived from Ethyl-2-hydroxy-quinoxaline-3-carboxylate. J Indian Chem Soc. 1986;63(4):427-9.
Finlay et al., Modulation of DNA repair by pharmacological inhibitors of the PIKK protein kinase family. Bioorg Med Chem Lett. Sep. 1, 2012;22(17):5352-9. doi: 10.1016/j.bmc1.2012.06.053. Epub Jul. 1, 2012.
Fokas et al., Targeting ATR in DNA damage response and cancer therapeutics. Cancer Treat Rev (2013), http://dx.doi.org/10.1016/j.ctrv.2013.03.002.
Fokas et al., Targeting ATR in vivo using the novel inhibitor VE-822 results in selective sensitization of pancreatic tumors to radiation. Cell Death Dis. Dec. 6, 2012;3:e441. doi: 10.1038/cddis.2012.181.
Gentili et al., Alpha2-adrenoreceptors profile modulation. 4. From antagonist to agonist behavior. J Med Chem. Jul. 24, 2008;51(14):4289-99. doi: 10.1021/jm800250z. Epub Jun. 25, 2008.
Hall-Jackson et al., ATR is a caffeine-sensitive, DNA-activated protein kinase with a substrate specificity distinct from DNA-PK. Oncogene. Nov. 18, 1999;18(48):6707-13.
Hickson et al., Identification and characterization of a novel and specific inhibitor of the ataxia-telangiectasia mutated kinase ATM. Cancer Res. Dec. 15, 2004;64(24):9152-9.

Hilton et al., Identification and characterisation of 2-aminopyridine inhibitors of checkpoint kinase 2. Bioorg Med Chem. Jan. 15, 2010;18(2):707-18. doi: 10.1016/j.bmc.2009.11.058. Epub Dec. 6, 2009.
Ho, Studies on the Synthesis of New 3-(3,5-Diamino-l-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines. Journal of the Chinese Chemical Society. 1999; 46:955-62.
Hubackova et al., Regulation of the PML tumor suppressor in drug-induced senescence of human normal and cancer cells by JAK/STAT-mediated signaling. Cell Cycle. Aug. 1, 2010;9(15):3085-99. doi: 10.4161/cc.9.15.12521. Epub Aug. 26, 2010.
Huntoon et al., ATR inhibition broadly sensitizes ovarian cancer cells to chemotherapy independent of BRCA status. Cancer Res. Jun. 15, 2013;73(12):3683-91. doi: 10.1158/0008-5472.CAN-13/0110. Epub Apr. 2, 2013.
Hussein, Novel Synthesis of Some New Pyrimido[1,6-a]pyrimidine and Pyrazolo[1,5-a]pyrimidine Derivatives. J Heterocyclic Chem. 2012;49(2):446-51.
Jiang et al., Synthesis and cytotoxicity evaluation of novel indolylpyrimidines and indolylpyrazines as potential antitumor agents. Bioorg Med Chem. May 2001;9(5):1149-54.
Katritzky et al., Efficient synthesis of 3,5-functionalized isoxazoles and isoxazolines via 1,3-dipolar cycloaddition reactions of 1-propargyl- and 1-allylbenzotriazoles. J Heterocyclic Chem. 2000;37(6):1505-10.
Kim et al., Substrate specificities and identification of putative substrates of ATM kinase family members. J Biol Chem. Dec. 31, 1999;274(53):37538-43.
Klicnar et al., Studien in der chinoxalinreihe III. Synthese, reaktionen und ir-spektren einiger 3-hydroxy-2-carboxymethylchinoxalin-derivate. Collection of Czechoslovak Chemical Communications. 1965;30(9):3092-101.
Kumpaty et al., Synthesis of N-methyl secondary amines. Synth Commun. 2003;33(8):1411-6.
Kurasawa et al., Revised Structure for the Product from the Reaction of 3-Hydrazinocarbonylmethylene-2-oxo-1,2,3,4-tetrahydroquinoxaline with Nitrous Acid. Chem. Pharm. Bull. 1984;32(10):4140-3.
Luo et al., Molecular dynamics-based self-organizing molecular field analysis on 3-amino-6-arylpyrazines as the ataxia telangiectasia mutated and Rad3 related (ATR) protein kinase inhibitors. Med Chem Res. Published online: Jun. 19, 2013. 12 pages.
McKenna et al., Evaluation of a potent and highly selective inhibitor of ATR kinase: an approach to selectively sensitize cancer cells to genotoxic drugs. Abstract. Mar. 31, 2012. 1page.
McKenna et al., Evaluation of the first potent and highly selective inhibitor of ATR inhibitor, VE-821: an approach to selectively sensitize cancer cells to ionizing radiation and hypoxia. Poster. Mar. 31, 2012. 1 page.
Middleton et al., ATR as a Therapeutic Target. In: Advances in DNA Repair in Cancer Therapy. Cancer Drug Discovery and Development. 2013;72:211-28.
Nakamura et al., Bimodal Chemiluminescence of 8-Chlorostyryl-6-phenylethynylimidazopyrazinone: Large Bathochromic Shift Caused by a Styryl Group at 8-Position. Tetrahedron Letters. 1998;39:301-4.
Otero et al., Synthesis of Acyclo-C-nucleoside Analogs from 2,3:4,5-Di-Oisopropylidene-D-xylose. J Carbohydrate Chem. 2005;24:809-29.
Otero et al., Synthesis of Iso-C-nucleoside Analogues from I-(Methyl 2-0-benzy1-4,6-O-benzylidene-3-deoxy-et-D-altropyranosid-3-yl)but-3-yn-2-ones. Z. Naturforsch. 2005; 60b:1175-85.
Pires et al., Targeting radiation-resistant hypoxic tumour cells through ATR inhibition. Br J Cancer. Jul. 10, 2012;107(2):291-9. doi: 10.1038/bjc.2012.265. Epub Jun. 19, 2012.
Pollard, Inhibition of the DNA Damage Response Kinase, ATR, as a Promising Anti-Cancer Approach. Presentation, Mar. 8, 2012. 28 pages.

(56) References Cited

OTHER PUBLICATIONS

Qi et al., Chemi- and Bio-Iuminescence of Coelenterazine Analogues with Phenyl Homologues at the C-2 Position. J Chem Soc. Perkin Trans 1. 1992:1607-11.
Ram et al., Synthesis of bioisosteric pyrazolo[1,5-a]pyrimidines as leishmanicides. Indian J Chemistry. 1995;34b:514-20.
Reaper et al., Evaluation of a Potent and Highly Selective Inhibitor of ATR Kinase: An Approach to Selectively Sensitize Cancer Cells to Genotoxic Drugs. 102nd AACR Annual Meeting. Orlando, 2011. Poster.
Reaper et al., Evaluation of a potent and highly selective inhibitor of ATR kinase: an approach to selectively sensitize cancer cells to genotoxic drugs. 102nd AACR Annual Meeting. Orlando, 2011. Abstract.
Reaper et al., Selective killing of ATM- or p53-deficient cancer cells through inhibition of ATR. Supplementary Information. Nature Chemical Biology. Apr. 13, 2011. doi:10.1038/nchembio.573. 26 pages.
Reaper et al., Selective Killing of ATM- or p53-deficient cancer cells through inhibition of ATR. Presentation, Nov. 29, 2011.
Reaper et al., Selective Killing of ATM- or p53-deficient cancer cells through inhibition of ATR. Presentation, Nov. 21, 2011.
Reaper et al., Selective killing of ATM- or p53-deficient cancer cells through inhibition of ATR. Nat Chem Biol. Apr. 13, 2011;7(7):428-30. doi: 10.1038/nchembio.573. Advance online publication.
Ried et al., Synthese neuer Heterocyclen ausgehend von Aminopyrazolen. Chemiker•Zeilung. 1989;181-3.
Saito et al., Synthesis and in vitro evaluation of botryllazine B analogues as a new class of inhibitor against human aldose reductase. Tetrahedron. 2009;65(15):3019-26.
Sarkaria et al., Inhibition of ATM and ATR kinase activities by the radiosensitizing agent, caffeine. Cancer Res. Sep. 1, 1999;59(17):4375-82.
Sevilla et al., Microwave-assisted synthesis of 1,3-dihydro-[1,2,5]thiadiazolo[3,4-b]pyrazine-2,2-dioxides. Tetrahedron Letters. 2006;47(48):8603-6.
Smith et al., Addition to Carbon—Hetero Multiple Bonds. Chapter 16. In: March's Advanced Organic Chemistry: Reactions, Mechanisms, and Structure, Sixth Edition. John Wiley & Sons, Inc. 2007. 26 pages.
Sugimoto et al., Imidazopteridines. I. Synthesis of Imidazo[1,2-c]pteridine and Its Alkyl Derivatives. Bull Chem Soc Japan. 1977;50(10):2744-7.
Vippagunta et al., Crystalline solids. Adv Drug Deliv Rev. May 16, 2001;48(1):3-26.
Ward et al., Histone H2AX is phosphorylated in an ATR-dependent manner in response to replicational stress. J Biol Chem. Dec. 21, 2001;276(51):47759-62. Epub Oct. 22, 2001.
Wolff, Burger's Medicinal Chemistry and Drug Discovery. Fifth Edition. vol. I: Principles and Practice. 1995;975-7.
Wuts et al., Protection for the Amino Group. Chapter 7. In: Greene's Protective Groups in Organic Synthesis, 4th Edition. John Wiley & Sons, Inc. 2007. 235 pages.
Wuts et al., Protection for the Carbonyl Group. Chapter 4. In: Greene's Protective Groups in Organic Synthesis, 4th Edition. John Wiley & Sons, Inc. 2007. 106 pages.
U.S. Appl. No. 14/098,667, filed Dec. 6, 2013, Boyall et al.
U.S. Appl. No. 13/531,467, filed Jun. 22, 2012, Storck et al.
U.S. Appl. No. 13/531,464, filed Jun. 22, 2012, Everitt et al.
U.S. Appl. No. 13/531,461, filed Jun. 22, 2012, MacCormick et al.
U.S. Appl. No. 14/098,606, filed Dec. 6, 2013, Ahmad et al.
U.S. Appl. No. 14/098,655, filed Dec. 6, 2013, Charrier et al.
U.S. Appl. No. 14/098,640, filed Dec. 6, 2013, Brenchley et al.
U.S. Appl. No. 14/098,602, filed Dec. 6, 2013, Charrier et al.
U.S. Appl. No. 13/167,654, filed Jun. 23, 2011, Charrier et al.
Office Communication, dated Jun. 27, 2014 for U.S. Appl. No. 14/098,640.

\* cited by examiner

FIGURE 1a: XRPD Compound I-1 (anhydrous free base)
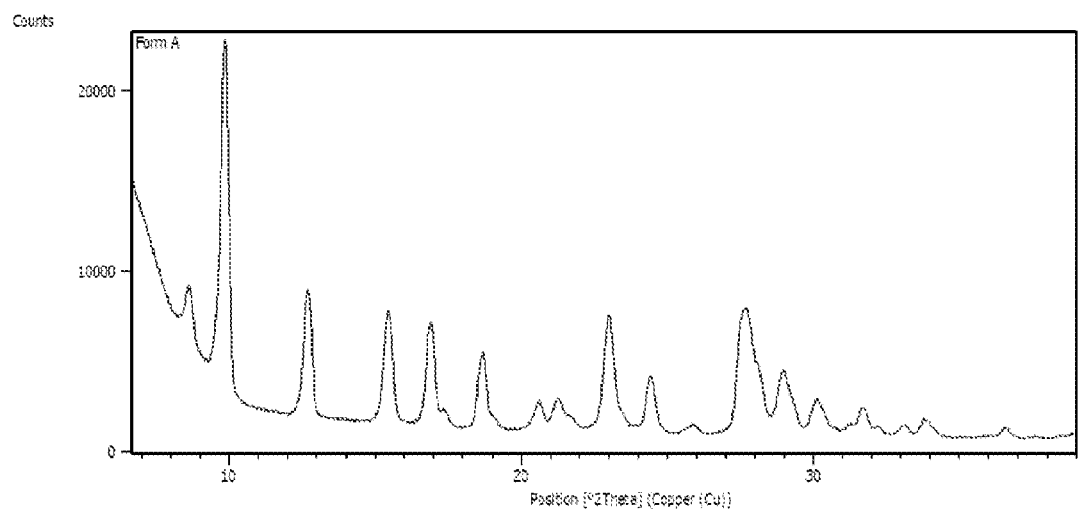
FIGURE 2a: TGA Compound I-1 (anhydrous free base)
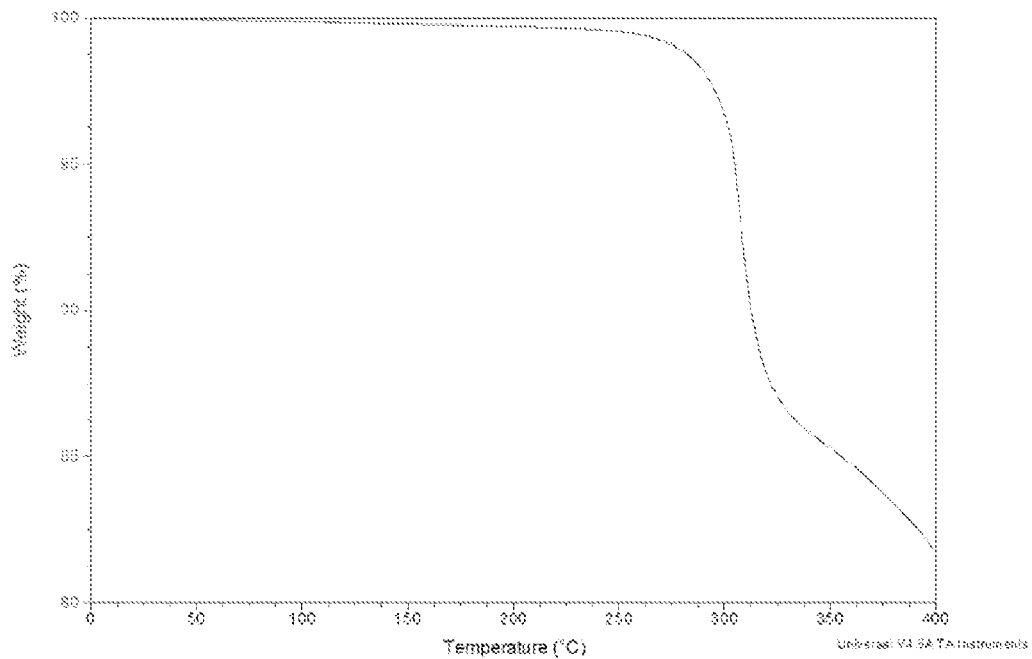

FIGURE 3a: DSC Compound I-1 (anhydrous free base)
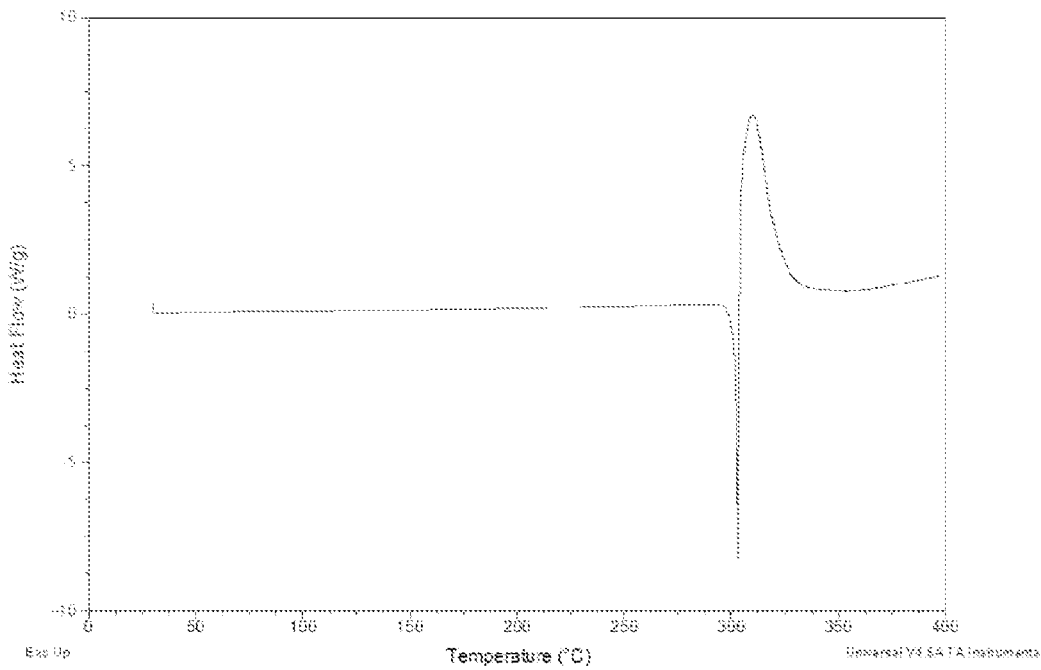
FIGURE 1b: XRPD Compound I-1 (hydrate)
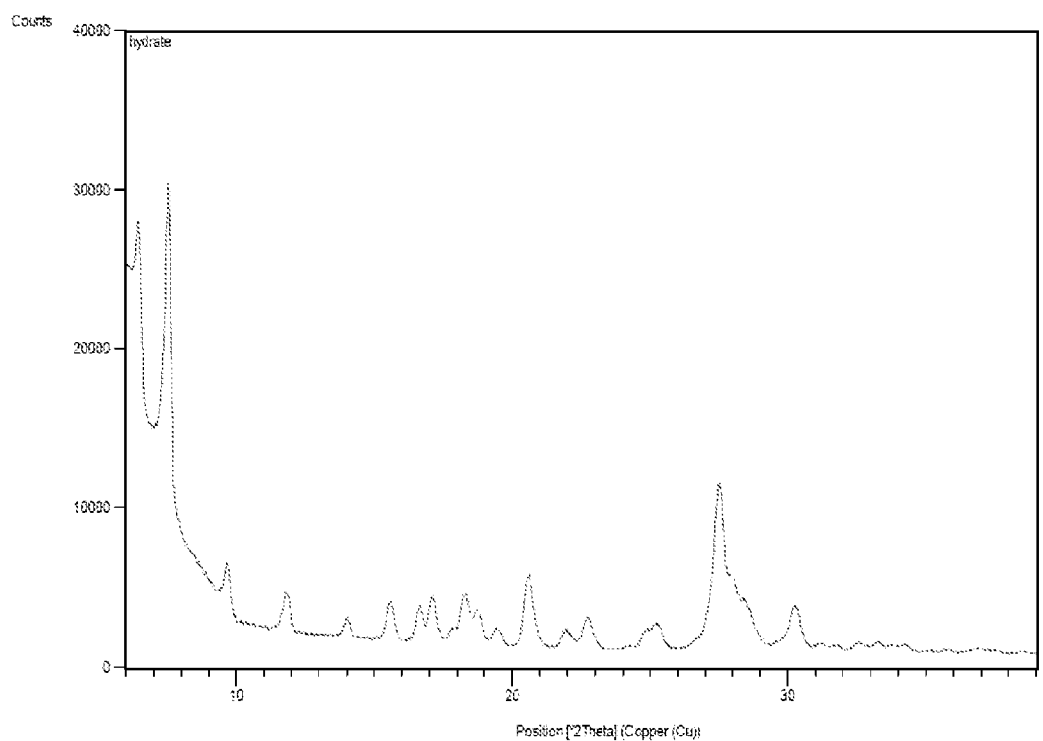

FIGURE 1c: XRPD Compound I-1 (tartaric acid)
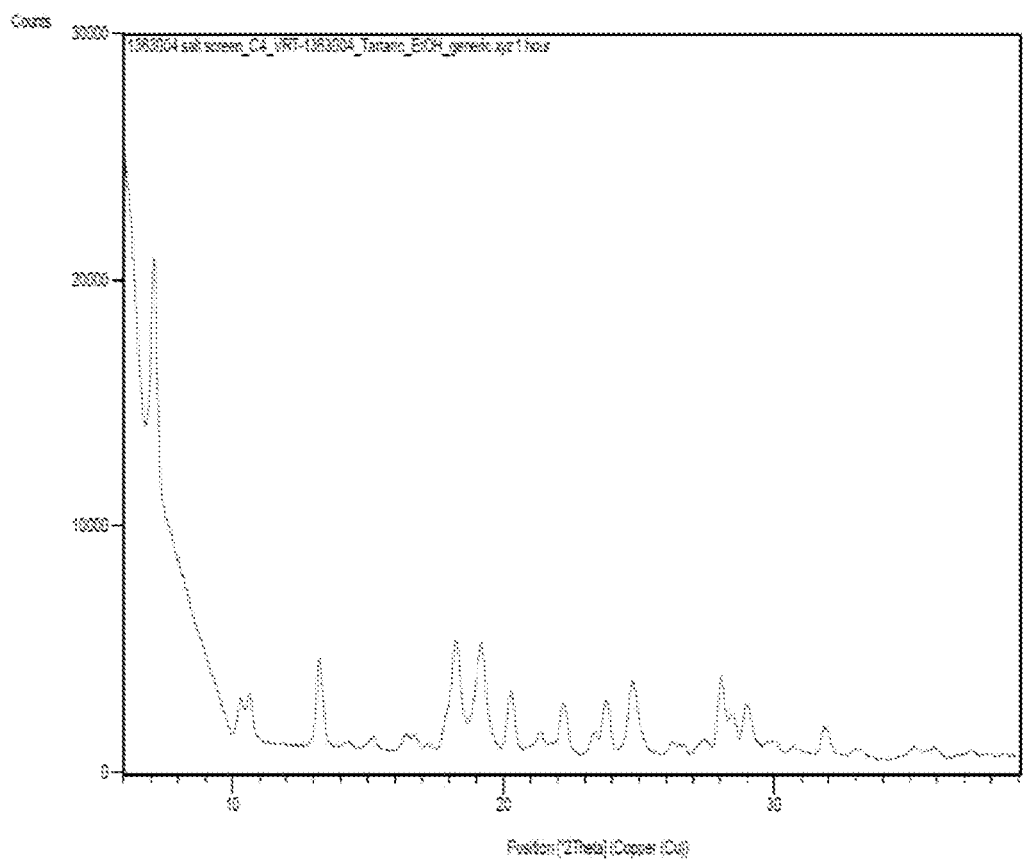
FIGURE 2c: TGA Compound I-1 (tartaric acid)
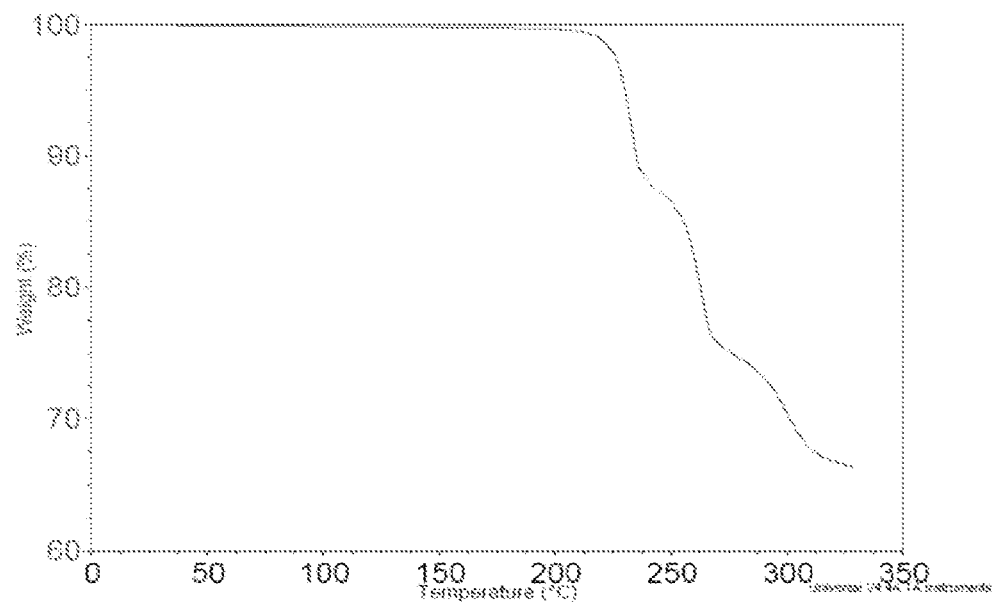

FIGURE 2b: TGA Compound I-1 (hydrate)
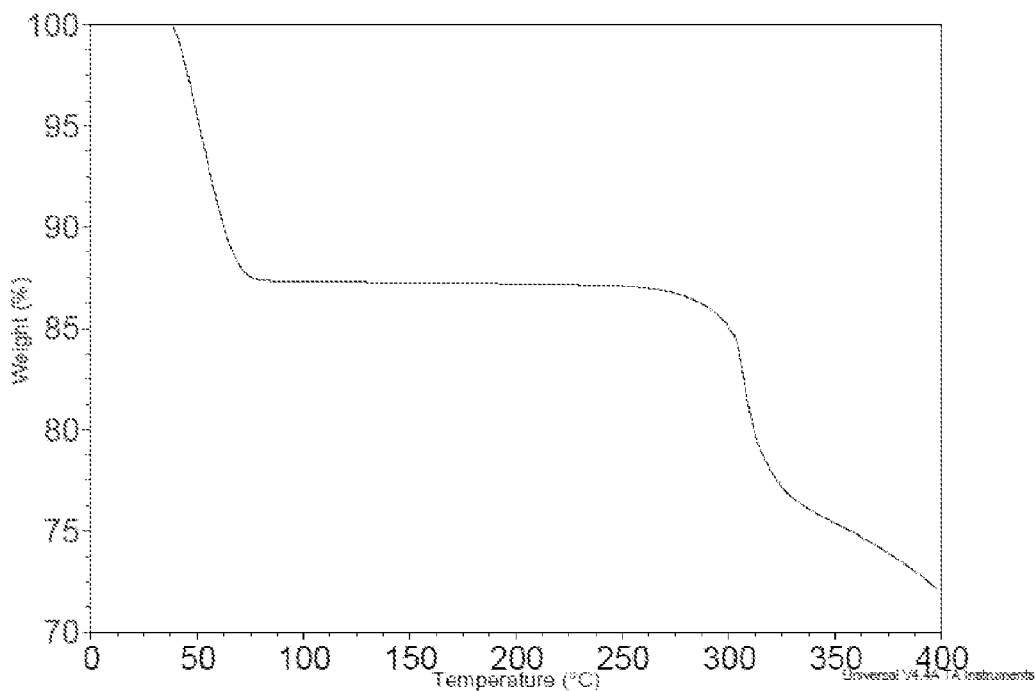
FIGURE 3b: DSC Compound I-1 (hydrate)
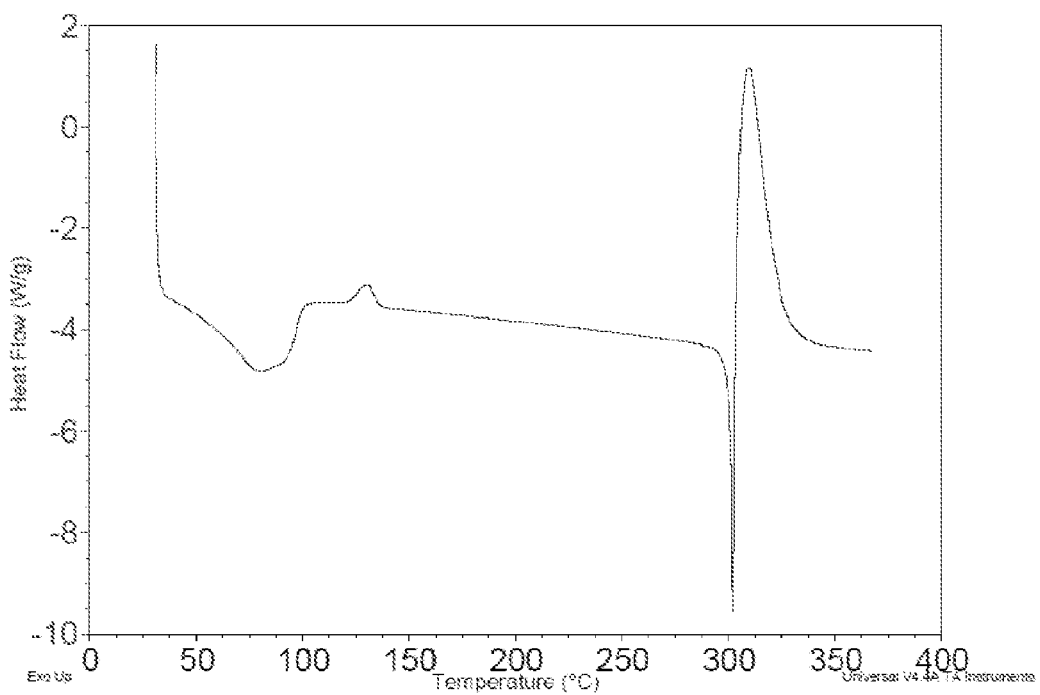

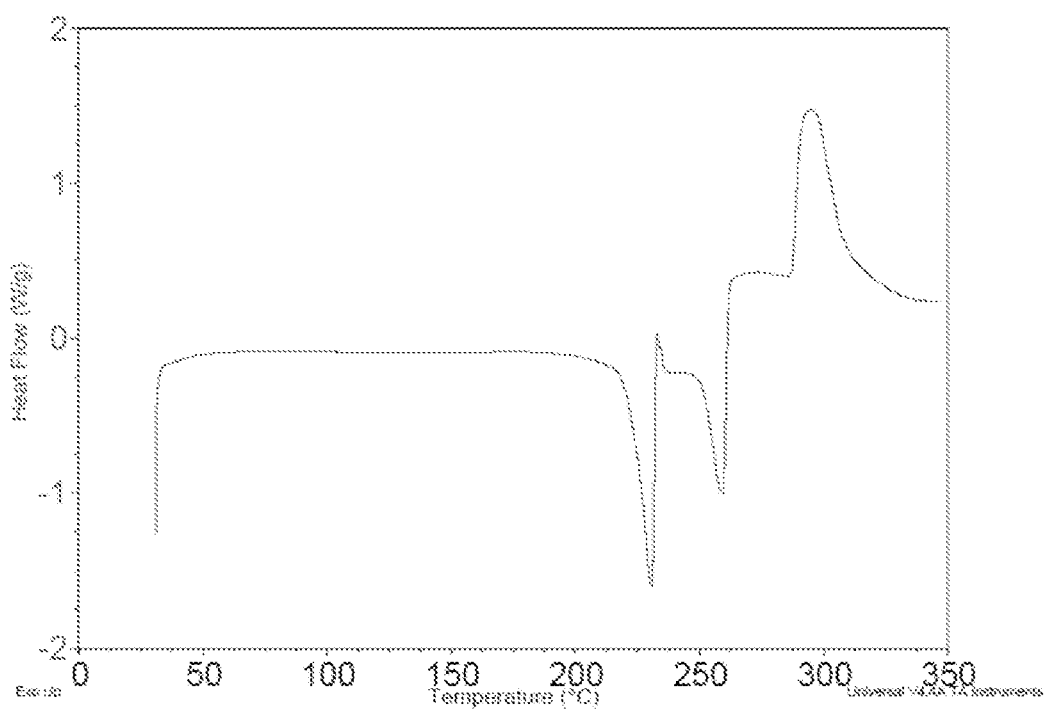
FIGURE 3c: DSC Compound I-1 (tartaric acid)

COMPOUNDS USEFUL AS INHIBITORS OF ATR KINASE

CROSS-REFERENCE TO RELATED APPLICATIONS

The present application claims the benefit under 35 U.S.C. §119 of U.S. Provisional Application No. 62/008,277, filed Jun. 5, 2014.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

For all of these reasons, there is a need for the development of potent and selective ATR inhibitors for the treatment of cancer, either as single agents or as combination therapies with radiotherapy or genotoxic chemotherapy. Furthermore, it would be desirable to have a synthetic route to ATR inhibitors that is amenable to large-scale synthesis and improves upon currently known methods.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

BRIEF DESCRIPTION OF THE FIGURES

FIG. 1*a*: XRPD Compound I-I anhydrous free base
FIG. 2*a*: TGA Compound I-1 anhydrous free base
FIG. 3*a*: DSC Compound I-1 anhydrous free base
FIG. 1*b*: XRPD Compound I-1 hydrate
FIG. 2*b*: TGA Compound I-1 hydrate
FIG. 3*b*: DSC Compound I-1 hydrate
FIG. 1*c*: XRPD Compound I-1 tartaric acid
FIG. 2*c*: TGA Compound I-1 tartaric acid
FIG. 3*c*: DSC Compound I-1 tartaric acid

SUMMARY OF THE INVENTION

The present invention relates to solid forms of ATR inhibitors as well as deuterated ATR inhibitors. The present invention also relates to processes and intermediates for preparing an aminopyrazolopyrimidine compound useful as a potent inhibitor of ATR kinase. Amino-pyrazolopyrimidine derivatives are useful as ATR inhibitors and are also useful for preparing ATR inhibitors.

One aspect of the invention provides a process for preparing compound I-1:

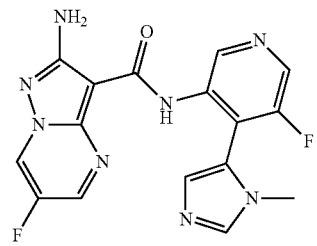

I-1

Another aspect of the present invention comprises a compound of formula I-A:

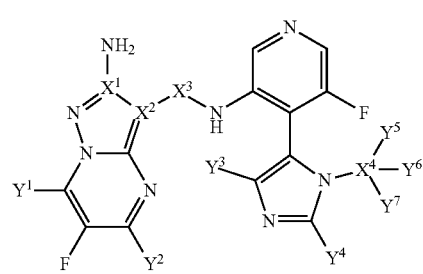

I-A or a pharmaceutically acceptable salt or derivative thereof, wherein:
each $Y^1$, $Y^2$, $Y^3$, $Y^4$, $Y^5$, $Y^6$, and $Y^7$ is independently hydrogen or deuterium; provided at least one of $Y^1$, $Y^2$, $Y^3$, $Y^4$, $Y^5$, $Y^6$, and $Y^7$ is deuterium;
each $X^1$, $X^2$, and $X^4$ is independently selected from $^{12}C$ or $^{13}C$; and
$X^3$ is independently selected from —$^{12}C(O)$— or —$^{13}C(O)$—.

Yet another aspect of the invention provides solid forms of a compound of formula I-1:

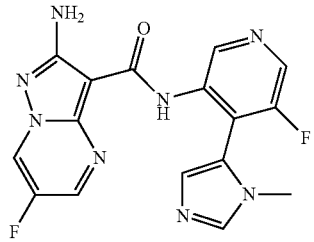

I-1

Other aspects of the invention are set forth herein.

DETAILED DESCRIPTION OF THE INVENTION

Processes

Another aspect of the present invention comprises a process for preparing a compound of formula I-1:

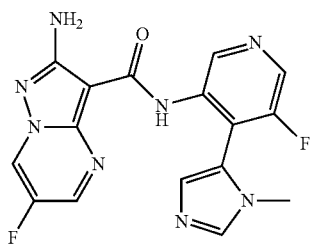

I-1 comprising the step of reacting the compound of formula 6b:

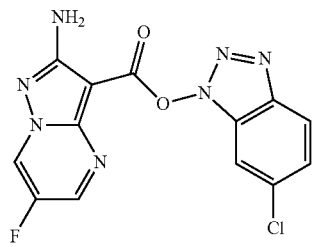

6b with a compound of formula 11:

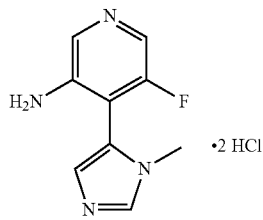

11 under suitable conditions to form an amide bond.

Suitable conditions for forming the amide bond comprises reacting the compound of formula 6b with the substituted 3-amino pyridine 11 in the presence of a solvent and an organic base. In one embodiment, the solvent can be selected from NMP, DMF or anisole (preferred). In another embodiment, the organic base is an aliphatic amine independently selected from triethylamine or DIPEA (preferred).

Still other embodiments of the present invention comprises a process for preparing the compound of formula 11:

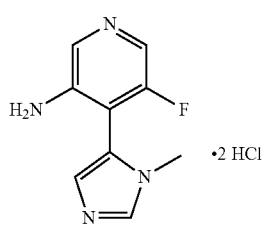

11 by reacting the compound of formula 9:

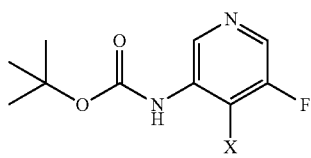

9 with a compound of formula 10:

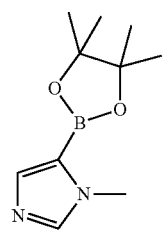

10 under suitable metal catalysed cross-coupling conditions to form an adduct
containing a protected amine group; and
subjecting the resulting adduct to suitable deprotection conditions.

Suitable metal catalysed cross-coupling conditions include a metal catalyst, a suitable solvent, and a suitable base. In some embodiments, the metal catalyst is a palladium catalyst. Examples of suitable palladium catalysts include, but are not limited to, $PdCl_2(PPh_3)_2$, $Pd(Ph_3)_4$, and $PdCl_2(dppf)$ (wherein each Ph is phenyl, and dppf is 1,1-bis(diphenylphosphino)ferrocene). Suitable bases include, but are not limited to, potassium phosphate, $K_2CO_3$, tBuOK and $Na_2CO_3$. Suitable solvents include, but are not limited to, DME, tetrahydrofuran, toluene, and ethanol.

Suitable deprotection conditions for removing the protecting group comprises reacting the protected species in the presence of a strong acid, such as HCl (preferred), HBr, sulfuric acid or trifluoroacetic acid.

Another embodiment provides a process for preparing a compound of formula 9:

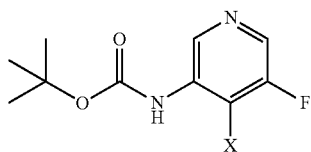

9 by reacting the compound of formula 8:

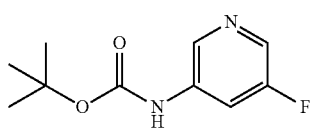

8 under suitable halogenation conditions.

Suitable halogenation conditions comprises reacting compound 8 in an aprotic solvent, in the presence of a strong base, and an electrophilic source of halogen. In one embodiment, the solvent can be selected from DCM, diethylether or THF (preferred). In another embodiment, the strong base is selected from tert-BuLi, sec-BuLi or n-BuLi (preferred). In yet another embodiment, the electrophilic species used to introduce the halogen atom can, for example, be selected from $I_2$ (preferred), $CF_3I$, diiodoethane, $Br_2$, $CBr_4$.

Still other embodiments of the present invention provides a process for preparing a compound of formula 8:

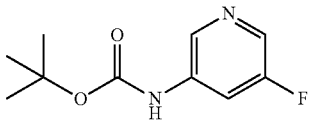

by reacting a compound of formula 7:

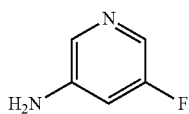

under suitable conditions to generate a protected amine group.

Suitable conditions for introducing the protecting group comprises reacting the amino species 7 in an aprotic solvent, in the presence of $Boc_2O$. Such reaction can be conducted in the presence of a base. In one embodiment, the solvent can be selected from diethylether or THF (preferred). In another embodiment, the strong base can be selected from DMAP, n-BuLi, LHMDS or NaHMDS (preferred).

Deuterated Compounds

Isotopes can be introduced on compound I-1 by selecting building blocks that contain the isotopic atoms (either commercial or that can be prepared according to the literature) and engaging them into a sequence similar to the novel and inventive process reported for the unlabelled material (described above).

Another aspect of the present invention provides a compound of Formula I-A:

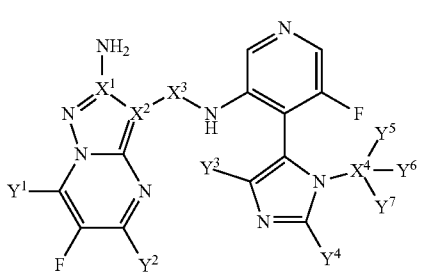

or a pharmaceutically acceptable salt or derivative thereof, wherein:
each $Y^1$, $Y^2$, $Y^3$, $Y^4$, $Y^5$, $Y^6$, and $Y^7$ is independently hydrogen or deuterium; provided at least one of $Y^1$, $Y^2$, $Y^3$, $Y^4$, $Y^5$, $Y^6$, and $Y^7$ is deuterium;
each $X^1$, $X^2$, and $X^4$ is independently selected from $^{12}C$ or $^{13}C$; and
$X^3$ is independently selected from —$^{12}C(O)$— or —$^{13}C(O)$—.

The following labelled building blocks, which can be used in the synthetic route for preparing the compound of Formula I-A, are all commercially available:
1,2-Di$^{13}$C-2-cyanoacetic acid;
1-$^{13}$C-2-cyano($^{13}$C)acetic acid ethyl ester;
2-$^{13}$C-2-cyano($^{13}$C)acetic acid ethyl ester;
1-(trideuteromethyl)-1H-imidazole;
2,4,5-trideutero-1-(methyl)-1H-imidazole; and
2,4,5-trideutero-1-(trideuteromethyl)-1H-imidazole.

Other labelled building blocks, which can be used in the synthetic route for preparing the compound of Formula I-A, are known to those skilled in the art. These may include, but are not limited to, the following labelled building blocks:
2-cyano($^{13}$C)acetic acid; Triplett et al., J Labelled Comp Radiopharm, 1978, 14(1), 35;
1-$^{13}$C-2-cyanoacetic acid; Matsumoto et al., Heterocycles, 1985, 23(8), 2041;
2-$^{13}$C-2-cyanoacetic acid; Baldwin et al., J Am Chem Soc, 1989, 111(9), 3319;
1-deutero-3-(diethylamino)-2-fluoroacrylaldehyde; Funabiki et al., Chem Lett, 1997, (8), 739;
2-deutero-1-(methyl)-1H-imidazole; Torregrosa et al., Tetrahedron, 2005, 61(47), 11148-11155;
4,5-dideutero-1-(methyl)-1H-imidazole; Pavlik et al., J. Org. Chem., 1991, 56(22), 6313-6320;
4,5-dideutero-1-(trideuteromethyl)-1H-imidazole; Mamer et al., Rapid Communications in Mass Spectrometry, 2005, 19(12), 1771-1774;
2-tritio-1-(methyl)-1H-imidazole; Buncel et al., Can. J. Chem., 1986, 64(6), 1240-1245;
2,4,5-trititrio-1-(methyl)-1H-imidazole; Grimmett, Scien of Synthesis, 2002, 325-528; and
1-($^{13}$C-methyl)-1H-imidazole; Van Thuijl et al., Organic Mass Spectrometry, 1973, 7(10), 1165-1172.

In one or more embodiments of the present invention, $Y^1$, $Y^2$, $Y^3$, and $Y^4$ are independently selected from deuterium or hydrogen; and $Y^5$, $Y^6$, and $Y^7$ are deuterium.

In some embodiments, $Y^1$ and $Y^2$ are independently selected from deuterium or hydrogen; and $Y^3$, $Y^4$, $Y^5$, $Y^6$, and $Y^7$ are deuterium.

In another embodiment, $Y^1$, $Y^2$, $Y^5$, $Y^6$, and $Y^7$ are independently selected from deuterium or hydrogen; and $Y^3$ and $Y^4$ are deuterium.

In other embodiments, $Y^1$, $Y^3$, and $Y^4$ are independently selected from deuterium or hydrogen; and $Y^2$, $Y^5$, $Y^6$, and $Y^7$ are deuterium.

In still other embodiments, $Y^1$, $Y^2$, $Y^3$, $Y^4$, $Y^5$, $Y^6$, and $Y^7$ are hydrogen; and $X^4$ is $^{13}C$.

In yet another embodiment $Y^1$, $Y^2$, $Y^3$, $Y^4$, $Y^5$, $Y^6$, and $Y^7$ are hydrogen; and $X^1$ and $X^4$ are $^{13}C$.

In some embodiments, $Y^1$, $Y^2$, $Y^3$, $Y^4$, $Y^5$, $Y^6$, and $Y^7$ are hydrogen; and $X^3$ is —$^{13}C(O)$—.

In another embodiment, $Y^1$, $Y^3$, $Y^4$, $Y^5$, $Y^6$, and $Y^7$ are hydrogen; $Y^2$ is deuterium; and $X^4$ is $^{13}C$.

In other embodiments, $Y^1$, $Y^2$, $Y^3$, and $Y^4$ are hydrogen; $Y^5$, $Y^6$, and $Y^7$ are deuterium; and $X^1$ is $^{13}C$.

In still other embodiments, $Y^1$, $Y^3$, $Y^4$, $Y^5$, $Y^6$, and $Y^7$ are hydrogen; $Y^2$ is deuterium; and $X^1$ is $^{13}C$.

In yet another embodiment, $Y^1$, $Y^2$, $Y^3$, $Y^5$, $Y^6$, and $Y^7$ are hydrogen; $Y^4$ is deuterium; and $X^1$ is $^{13}C$.

In another embodiment, Y1 is hydrogen; $Y^2$, $Y^3$, $Y^4$, $Y^5$, $Y^6$, and $Y^7$ are deuterium; $X^2$ is $^{13}C$; and $X^3$ is —$^{13}C(O)$—.

In another example, the compounds of formula I-A of this invention are represented in Table 1. It will be appreciated by those skilled in the art that the compounds of the present invention may be represented in varying tautomeric forms.

TABLE 1
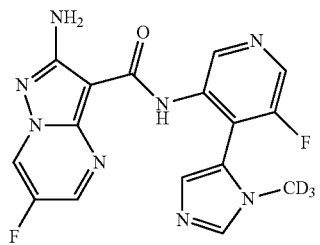 [SMILES: [2H]C([2H])([2H])n1cncc1-c1c(F)cncc1NC(=O)c1c(N)nn2cc(F)cnc12] I-2
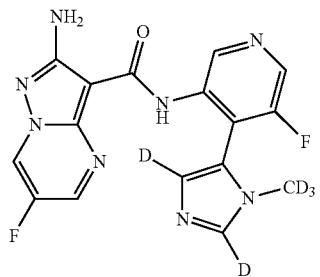 [SMILES: [2H]c1nc([2H])n(C([2H])([2H])[2H])c1-c1c(F)cncc1NC(=O)c1c(N)nn2cc(F)cnc12] I-3
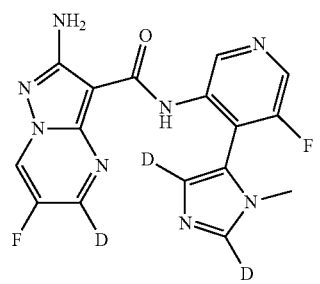 [SMILES: [2H]c1nc2c(C(=O)Nc3cncc(F)c3-c3c([2H])nc([2H])n3C)c(N)nn2cc1F] I-4
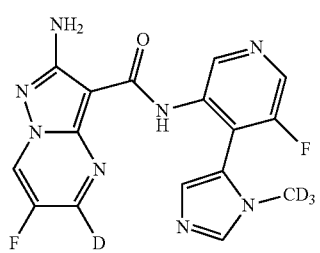 [SMILES: [2H]c1nc2c(C(=O)Nc3cncc(F)c3-c3cncn3C([2H])([2H])[2H])c(N)nn2cc1F] I-5
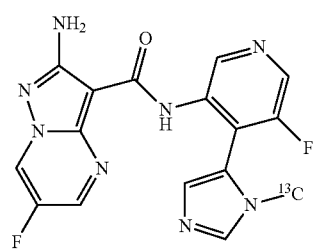 [SMILES: [13CH3]n1cncc1-c1c(F)cncc1NC(=O)c1c(N)nn2cc(F)cnc12] I-6
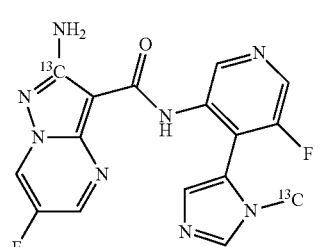 I-7
TABLE 1-continued
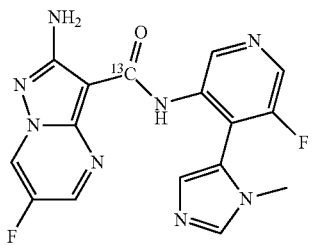 [SMILES: Cn1cncc1-c1c(F)cncc1N[13C](=O)c1c(N)nn2cc(F)cnc12] I-8
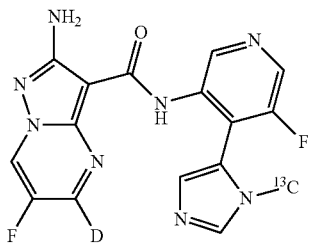 [SMILES: [2H]c1nc2c(C(=O)Nc3cncc(F)c3-c3cncn3[13CH3])c(N)nn2cc1F] I-9
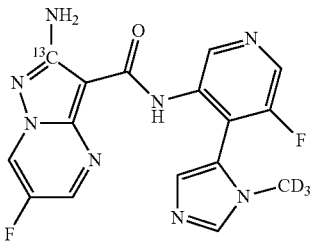 [SMILES: [2H]C([2H])([2H])n1cncc1-c1c(F)cncc1NC(=O)c1c2ncc(F)cn2n[13c]1N] I-10
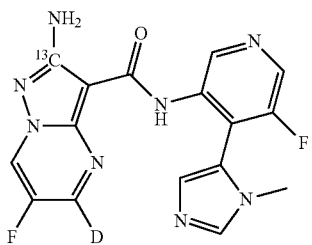 [SMILES: [2H]c1nc2c(C(=O)Nc3cncc(F)c3-c3cncn3C)[13c](N)nn2cc1F] I-11
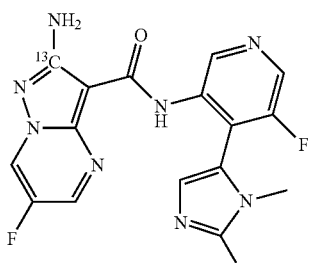 I-12
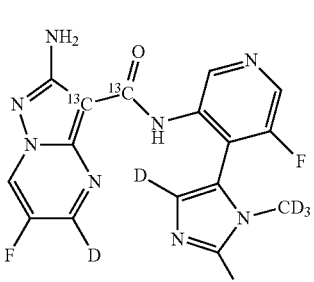 I-13

Solid Forms

Another aspect of the present invention provides a solid form of a compound of formula I-1:

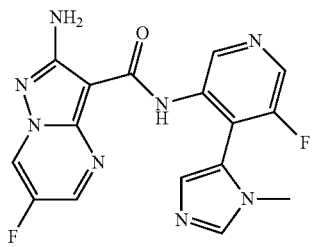

I-1 wherein, the form is selected from the group consisting of Compound I-1 anhydrous free base, Compound I-1 hydrate, or Compound I-1 tartaric acid.

Compound I-1 Anhydrous Free Base

In some aspects of the present inventions, the solid form is Compound I-1 anhydrous free base. In another aspect of the present invention, the solid form is crystalline Compound I-1 anhydrous free base. In some embodiments, the solid form is characterized by one or more peaks expressed in 2-theta±0.2 at about 9.9, 12.8, 15.4, 17.0, 23.1, 27.8, 29.0, and 30.1 degrees in an X-Ray powder diffraction pattern obtained using Cu K alpha radiation. In other embodiments, the solid form is characterized as having an X-ray powder diffraction pattern substantially the same as that shown in FIG. 1a.

Compound I-1 Hydrate

In some aspects of the present invention, the solid form is Compound I-1 hydrate. In another aspect of the present invention, the solid form is crystalline Compound I-1 hydrate. In other embodiments, the crystalline Compound I-1 hydrate has a Compound I-1 to water ratio of 1:3. In still other embodiments, Compound I-1 hydrate is characterized by a weight loss of from about 12.6% in a temperature range from about 40° C. and about 100° C. In some embodiments, the solid form is characterized by one or more peaks expressed in 2-theta±0.2 at about 27.5, 20.6, and 9.7 degrees in an X-Ray powder diffraction pattern obtained using Cu K alpha radiation. In yet other embodiments, the solid form is characterized as having an X-ray powder diffraction pattern substantially the same as that shown in FIG. 1b.

Compound I-1 Tartaric Acid

In some aspects of the present invention, the solid form is Compound I-1 tartaric acid. In another aspect of the present invention, the solid form is crystalline Compound I-1 tartaric acid. In other embodiments, the crystalline Compound I-1 tartaric acid has a Compound I-1 to tartaric acid ratio of 1:1. In some embodiments, the solid form is characterized by one or more peaks expressed in 2-theta±0.2 at about 7.1, 18.3, and 13.2 degrees in an X-Ray powder diffraction pattern obtained using Cu K alpha radiation. In yet other embodiments, the solid form is characterized as having an X-ray powder diffraction pattern substantially the same as that shown in FIG. 1c.

For purposes of this application, it will be understood that the terms embodiment, example, and aspect are used interchangeably.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^w$ can be bonded to any position on the pyridyl ring. For bicyclic rings, a bond drawn through both rings indicates that the substituent can be bonded from any position of the bicyclic ring. In example ii below, for instance, J$^w$ can be bonded to the 5-membered ring (on the nitrogen atom, for instance), and to the 6-membered ring.

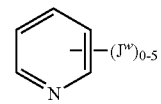

i

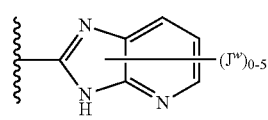

ii

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$— cyclopropyl, CH$_2$CH$_2$CH (CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

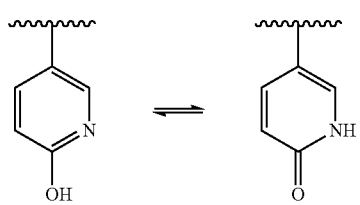 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e., both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

The term "cross-coupling reaction", as used herein, refers to a reaction in which a carbon-carbon bond is formed with the aid of a metal catalyst. Usually, one of the carbon atoms is bonded to a functional group (a "cross-coupling group") while the other carbon atom is bonded to a halogen. Examples of cross coupling reactions include, but are not limited to, Suzuki couplings, Stille couplings, and Negishi couplings.

The term "cross-coupling group", as used herein, refers to a functional group capable of reacting with another functional group (e.g., halo) in a cross coupling reaction to form a carbon-carbon ("C—C") bond. In some embodiments, the C—C bond is formed between two aromatic groups.

The term "cross coupling condition", as used herein, refers to the chemical conditions (e.g., temperature, length of time of reaction, volume of solvent required) required in order to enable the cross coupling reaction to occur.

Examples of cross-coupling groups and their respective cross-coupling conditions include, but are not limited to, boronic acids and boronic esters with Suzuki coupling conditions, SnBu$_3$ (Bu: butyl) with Stille coupling conditions, and ZnX (X: halogen) with Negishi coupling conditions.

All three of these coupling conditions typically involve the use of a catalyst, a suitable solvent, and optionally a base. Suzuki coupling conditions involve the use of a palladium catalyst and a suitable solvent. Examples of suitable palladium catalysts include, but are not limited to, PdCl$_2$(PPh$_3$)$_2$, Pd(Ph$_3$)$_4$, and PdCl$_2$(dppf) (wherein each Ph is phenyl, and dppf is 1,1-bis(diphenylphosphino)ferrocene). Suitable bases include, but are not limited to, K$_2$CO$_3$ and Na$_2$CO$_3$. Suitable solvents include, but are not limited to, tetrahydrofuran, toluene, and ethanol.

Stille coupling conditions involve the use of a catalyst (usually palladium, but sometimes nickel), a suitable solvent, and other optional reagents. Examples of suitable catalysts include, but are not limited to, PdCl$_2$(PPh$_3$)$_2$, Pd(Ph$_3$)$_4$, and PdCl$_2$(dppf). Suitable solvents include, but are not limited to, tetrahydrofuran, toluene, and dimethylformamide.

Negishi coupling conditions involve the use of a catalyst (palladium or nickel) and a suitable solvent. Examples of suitable catalysts include, but are not limited to $Pd_2(dba)_3$, $Ni(PPh_3)_2Cl_2$, $PdCl_2(PPh_3)_2$, and $Pd(Ph_3)_4$ (where "dba" is tris(dibenzylideneacetone)dipalladium). Suitable solvents include, but are not limited to, tetrahydrofuran, toluene, and dimethylformamide.

Suzuki, Stille, and Negishi conditions are known to one skilled in the art and are described in more detail in a variety of references, including "March's Advanced Organic Chemistry".

As would be understood by one skilled in the art, cross-coupling groups are formed from coupling group precursors. A coupling group precursor is a reagent or group of reagents used to form a cross-coupling group. Examples include, but are not limited to, bis(pinacolato)diborane for the formation of boronate esters, trimethylborates for the formation of boronic acids, $Bu_3SnCl$ for the formation of stannanes, and $ZnCl_2$ for the formation zincates in Negishi coupling reactions. Examples of suitable coupling group formation conditions include, but are not limited to, making boronic esters via palladium-mediated catalysis; making boronic acids by hydrolyzing boronic esters; making stannanes via a two step process: 1) halogen metal exchange followed by 2) transmetallation with $Bu_3SnCl$ and making zincates via a two step process: 1) halogen metal exchange followed by 2) addition of $ZnCl_2$.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

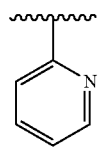

also represents

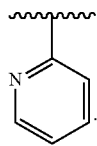

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

"D" and "d" both refer to deuterium.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

As used herein "crystalline" refers to a solid that has a specific arrangement and/or conformation of the molecules in the crystal lattice.

As used herein the term "amorphous" refers to solid forms that consist of disordered arrangements of molecules and do not possess a distinguishable crystal lattice.

As used herein, the term "solvate" refers to a crystalline solid adduct containing either stoichiometric or nonstoichiometric amounts of a solvent incorporated within the crystal structure. If the incorporated solvent is water, such adduct is referred to as a "hydrate".

ABBREVIATIONS

The following abbreviations are used:
DMSO dimethyl sulfoxide
DCM dichloromethane
ATP adenosine triphosphate
TFA trifluoroacetic acid
$^1$HNMR proton nuclear magnetic resonance
HPLC high performance liquid chromatography
LCMS liquid chromatography-mass spectrometry
Rt retention time
XRPD X-Ray Powder Diffraction
DSC Differential scanning calorimetry
TGA Thermogravimetric analysis
RT room temperature
NMP N-methyl-2-pyrrolidone
Bp boiling point
DMF dimethylformamide
PTSA p-Toluenesulfonic acid
DIPEA N,N-diisopropylethylamine
HOBT hydroxybenzotriazole
HATU 1-[Bis(dimethylamino)methylene]-1H-1,2,3-triazolo[4,5-b]pyridinium 3-oxid hexafluorophosphate
TBTU 2-(1H-benzotriazole-1-yl)-1,1,3,3-tetramethyluronium tetrafluoroborate
T3P Propylphosphonic anhydride
COMU 1-[(1-(Cyano-2-ethoxy-2-oxoethylideneaminooxy)-dimethylamino-morpholino)]uroniumhexafluorophosphate
TCTU [(6-chlorobenzotriazol-1-yl)oxy-(dimethylamino)methylene]-dimethyl-ammonium tetrafluoroborate
HBTU O-Benzotriazole-N,N,N',N'-tetramethyl-uronium-hexafluoro-phosphate
DME Dimethoxyethane
THF tetrahydrofuran
TMEDA tetramethylethylenediamine
NaHMDS sodium hexamethyldisilazane
LHMDS Lithium bis(trimethylsilyl)amide
Processes Processes and compounds described herein are useful for producing ATR inhibitors that contain an aminopyrazolopyrimidine core. The general synthetic procedures shown in schemes herein are useful for generating a wide array of chemical species which can be used in the manufacture of pharmaceutical compounds.

4 is subjected to hydrolytic conditions that are known to those skilled in the art. For example, treatment of 4 with phenylsilane or 4-methylbenzenesulfinate in the presence of a catalytic amount of palladium (e.g., $Pd(PPh_3)_4$) leads to the

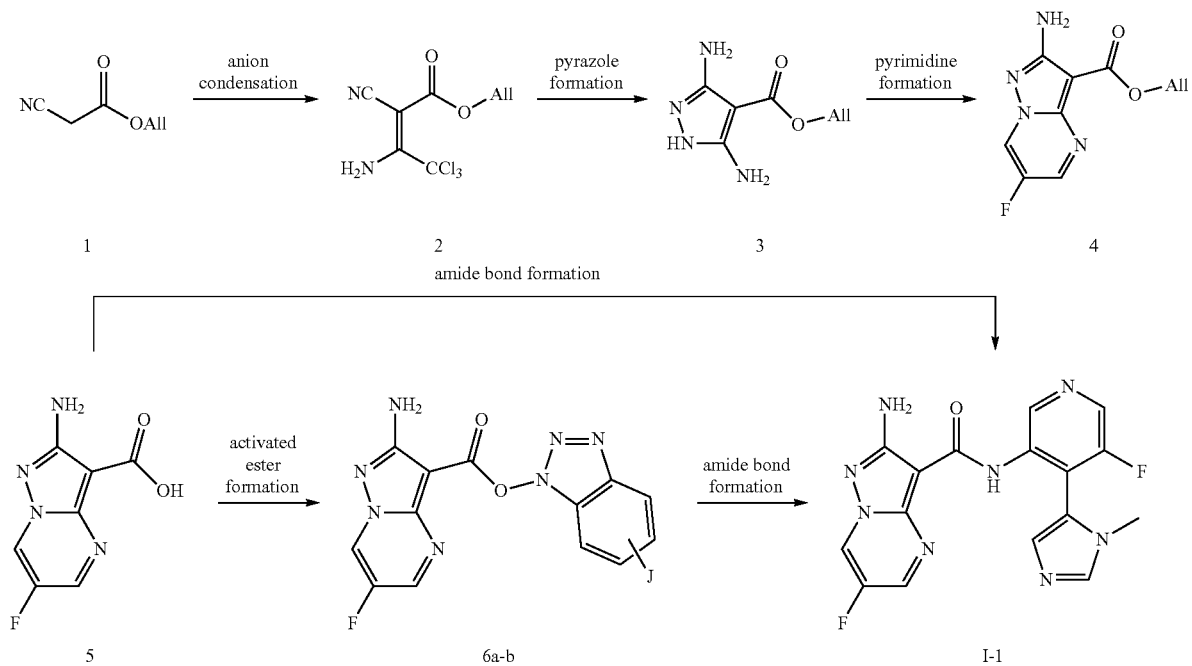

SCHEME A

Compounds of this invention can be synthesised according to methods similar to the one depicted in Scheme A.

Step 1

The anion of commercially available allyl cyanoacetate 1 can react with, e.g., trichloroacetonitrile to provide intermediate 2. In the anion condensation step, the anion of commercially available allyl cyanoacetate 1 can be generated with a base such as potassium acetate in an appropriate solvent such as an alcohol (e.g., isopropylalcohol). The anion then reacts with trichloroacetonitrile at room temperature.

Step 2

Intermediate 2 then reacts with hydrazine to form the diaminopyrazole 3. In the pyrazole formation step, intermediate 2 is reacted with hydrazine (or its hydrate) in an aprotic solvent, such as DMF, to provide the diaminopyrazole 3. The reaction occurs under basic conditions (e.g., in the presence of potassium acetate or AcONa) with heating (e.g., ≥110° C.) to ensure complete cyclisation.

Step 3

Intermediate 3 can further be condensed with a dielectrophilic coupling partner to form the pyrimidine 4. In the pyrimidine formation step, intermediate 3 is reacted with a 1,3-dielectrophilic species (e.g., a 1,3-dialdehyde or a 3-(dialkylamino)-prop-2-enal) in various types of solvents (e.g., DMF or DMSO/water) to furnish the bicyclic cores 4. When one or two of the electrophilic centers is protected/masked (e.g., aldehyde masked as a ketal), introduction of a sulfonic acid (e.g., PTSA) is required to liberate the reactive functional group.

Step 4

Deprotection, e.g, via hydrolysis, of the allyl ester leads to the carboxylic acids 5. In the deprotection step, compound 4 is subjected to hydrolytic conditions that are known to those skilled in the art. For example, treatment of 4 with phenylsilane or 4-methylbenzenesulfinate in the presence of a catalytic amount of palladium (e.g., $Pd(PPh_3)_4$) leads to the formation of the corresponding carboxylic acid 5. Alternatively, compounds 4 could be treated with aqueous alkali (e.g., NaOH, LiOH, or KOH) to produce acids 5.

Step 5

In the activated ester formation step, the carboxylic acids 5 are reacted with amide coupling agents known to those skilled in the art. Suitable amide coupling partners include, but are not limited to TBTU, TCTU, HATU, T3P, and COMU. When the coupling agent is chosen appropriately, the reactions can proceed rapidly (~1 hr.) at room temperature in the presence of an organic base such as an aliphatic amine (e.g., triethylamine, DIPEA) to provide the activated esters 6a-b. For example, when the amide coupling agents TBTU [J=H] or TCTU[J=Cl] are used, compounds 6a-b are obtained readily by filtration of the reaction mixture.

Formation of the activated esters 6a-b prior to the amide bond formation to prepare I-A is generally preferred, although a direct conversion of 5 into the compounds of formula I-A of this invention is also possible. Alternative activated esters can also be utilised (isolated or formed in situ) and will be known to those skilled in the art (e.g., using TBTU, TCTU, HATU, T3P, COMU coupling agents).

Step 6

In the amide bond formation step, activated esters 6a-b can react with substituted 3-aminopyridine 11 to provide compound I-1 of this invention. The reaction conditions for the amide coupling are in a solvent (e.g. anisole, NMP, pyridine, DMF, etc . . . ) with heating (e.g., ≥90° C.).

Alternatively, the two steps described above can be combined: carboxylic acid 5 can be used as starting points for the amide bond formation, the activated esters being generated in situ, using the same amide couplings agents as those described above. Compounds of this invention are isolated in a similar manner to the one described above.

PREPARATIONS AND EXAMPLES

All commercially available solvents and reagents were used as received. Microwave reactions were carried out using a CEM Discovery microwave. Flash Chromatography, e.g., was carried out on an ISCO© Combiflash® Companion™ system eluting with a 0 to 100% EtOAc/petroleum ether gradient. Other methods known in the art were also utilized to perform Flash Chromotography. Samples were applied pre-absorbed on silica. Where stated, supercritical fluid chromatography (SFC) was performed on a Berger Minigram SFC machine. All $^1$H NMR spectra were recorded using a Bruker Avance III 500 instrument at 500 MHz. MS samples were analyzed on a Waters SQD mass spectrometer with electrospray ionization operating in positive and negative ion mode. Samples were introduced into the mass spectrometer using chromatography. All final products had a purity ≥95%, unless specified otherwise in the experimental details. HPLC purity was measured on a Waters Acquity UPLC system with a Waters SQD MS instrument equipped with a Waters UPLC BEH C8 1.7 μm, 2.1×50 mm column and a Vanguard BEH C8 1.7 μm, 2.1×5 mm guard column.

As used herein, the term "Rt(min)" refers to the HPLC retention time, in minutes, associated with the compound. Unless otherwise indicated, the HPLC methods utilized to obtain the reported retention times are as described below:
HPLC Method B
Instrument: Waters Acquity UPLC-MS;
Column: Waters UPLC BEH C8 1.7 μm, 2.1×50 mm with Vanguard BEH C8 1.7 μm, 2.1×5 mm guard column;
Column temperature: 45° C.;
Mobile Phase A: 10 mM ammonium formate in water: acetonitrile 95:5, pH 9;
Mobile Phase B: acetonitrile;
Detection: 210-400 nm;
Gradient: 0-0.40 min: 2% B, 0.40-4.85 min: 2% B to 98% B, 4.85-4.90 min: 98% B to 2% B, 4.90-5.00 min: hold at 2% B;
Flow rate: 0.6 mL/minute.

Preparation 1: Allyl 3,5-diamino-1H-pyrazole-4-carboxylate

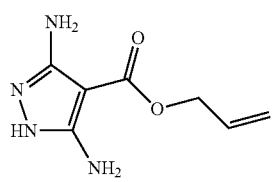

3

Step 1: allyl 3-amino-4,4,4-trichloro-2-cyanobut-2-enoate 2

To a solution of KOAc (589.4 g, 6.006 mol) in isopropanol (3 L) was added allyl cyanoacetate (429.4 g, 403.2 mL, 3.432 mol) and the reaction mixture was cooled to 5° C. Trichloroacetonitrile (495.5 g, 3.432 mol) was added in 50 mL portions, maintaining temperature below 15° C. The reaction mixture was then allowed to warm to 20° C. and stirred for 3 hr. Water (~4 L) was added to dissolve the inorganic materials and precipitate out the desired product. The mixture was stirred for 20 minutes and the solid was isolated by filtration under vacuum. This solid was filtered, washed with water (2×0.5 L) and dried in a vacuum oven overnight at 40° C. to afford allyl 3-amino-4,4,4-trichloro-2-cyanobut-2-enoate 2 as an off-white powder (787 g, 85%).

Step 2: Allyl 3,5-diamino-1H-pyrazole-4-carboxylate 3

To a suspension of allyl 3-amino-4,4,4-trichloro-2-cyanobut-2-enoate 2 (619 g, 2.297 mol) and KOAc (676.3 g, 6.891 mol) in DMF (2.476 L) at 0° C. was slowly added hydrazine hydrate (172.5 g, 167.6 mL, 3.446 mol) over 15 min. The reaction mixture was then stirred at ambient temperature for 2 hr., at which stage $^1$H NMR shows complete consumption of the starting material. Reaction mixture was then heated overnight at 110° C. before being allowed to cool to ambient and stirred for another 48 hr. The mixture was filtered through a sintered glass funnel to remove the precipitated solid and the filtrate was evaporated under reduced pressure to give a thick liquid. DCM (approx 2 L) was added, and the mixture filtered again to remove additional solids that have precipitated. The filtrate was purified through a 1 kg silica gel plug (gradient of DCM/MeOH as an eluent), and the solvent was removed to afford an orange solid which was suspended in acetonitrile and heated at about 70° C. until all the solid went into solution, at which point the solution was allowed to cool to ambient temperature, then to 2° C. The precipitate that formed was isolated by filtration under vacuum, washed with chilled MeCN (~50 mL) and dried to constant mass in a vacuum oven to furnish the title compound as an off-white powder (171.2 g, 41%).

Preparation 2a: 1H-benzo[d][1,2,3]triazol-1-yl 2-amino-6-fluoropyrazolo[1,5-a]pyrimidine-3-carboxylate

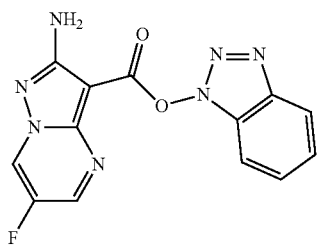

6a

Step 1: allyl 2-amino-6-fluoro-pyrazolo[1,5-a]pyrimidine-3-carboxylate 4

To a suspension of allyl 3,5-diamino-1H-pyrazole-4-carboxylate 3 (42.72 g, 234.5 mmol) in DMSO (270.8 mL)/Water (270.8 mL), was added p-TsOH hydrate (46.72 g, 245.6 mmol) and 3-(diisopropylamino)-2-fluoro-prop-2-enal (described in *Tetrahedron Letters*, 33(3), 357-60; 1992) (38.69 g, 223.3 mmol). The reaction mixture was heated to 100° C. for 3 hr. during which time a solid slowly precipitated out of solution. The orange suspension was allowed to cool down to RT overnight. The solid was filtered, washed with water and dried under vacuum to give allyl 2-amino- 6-fluoro-pyrazolo[1,5-a]pyrimidine-3-carboxylate 4 as a sand solid (45.05 g, 85% yield).

Step 2: 2-amino-6-fluoro-pyrazolo[1,5-a]pyrimidine-3-carboxylic acid 5

To a suspension of allyl 2-amino-6-fluoro-pyrazolo[1,5-a]pyrimidine-3-carboxylate 4 (45 g, 190.5 mmol) in DCM (1.35 L) was added phenylsilane (41.23 g, 46.96 mL, 381.0 mmol), followed by Pd(PPh$_3$)$_4$ (8.805 g, 7.620 mmol). The reaction was stirred at room temperature for 2 hr. 30 min. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-fluoro-pyrazolo[1,5-a]pyrimidine-3-carboxylic acid 5 as a light yellow solid (37.77 g, 100% yield).

In an alternative method, 4-methylbenzenesulfinate (anhydrous, 1.2 eqv, 22.6 g, 127 mmol) was suspended in dry DMSO (20 vol, 500 ml). The stirred mixture was warmed to 30° C. under a nitrogen atmosphere. Upon complete dissolution Pd(PPh$_3$)$_4$ (2 mol %, 2.4 g, 2.1 mmol) was added. The mixture was stirred for 10 min at 25-30° C. after which time a turbid yellow solution was present. Allyl 2-amino-6-fluoro-pyrazolo[1,5-a]pyrimidine-3-carboxylate 4 (25 g, 105.8 mmol) was added portionwise, maintaining the temperature at 25-30° C. Once addition was complete the cloudy solution was stirred until the reaction was complete by HPLC (2-3 hrs). A heavy precipitate formed after 15 minutes post addition of the substrate. The mixture became thicker as the reaction proceeded. The reaction mixture was diluted with water (125 ml) and 2M HCl (66 ml) was added slowly, maintaining the temperature at 25-30° C. The slurry was stirred for 30 minutes, then filtered. The filtration was slow (2 hrs). The resulting solid was washed with water, then dried on the sinter. The solid was slurried in DCM (8 vol) for 1 hr. The solid was filtered (rapid filtration) and washed with DCM. The solid was re-slurried in chloroform (8 vol) for 1 hr. The acid was filtered and dried on the sinter. It was further dried in a vacuum oven at 50° C. for 24 hrs. The product 5 was obtained as an off-white solid (18.6 g, 85%); $^1$H NMR (500 MHz, DMSO-d6) δ 12.14 (1H, brs), 9.31 (1H, dd), 8.69 (1H, m), 6.47 (2H, brS); 19F NMR (500 MHz, DMSO-d6) δ -153.65; MS (ES+) 197.1.

Step 3: 1H-benzo[d][1,2,3]triazol-1-yl 2-amino-6-fluoropyrazolo[1,5-a]pyrimidine-3-carboxylate 6a To a suspension of 2-amino-6-fluoro-pyrazolo[1,5-a]pyrimidine-3-carboxylic acid 5 (20 g, 102.0 mmol) in chloroform (300 mL) was added Et$_3$N (11.35 g, 15.63 mL, 112.2 mmol). The suspension was stirred for ~5 mins and then (benzotriazol-1-yloxy-dimethylamino-methylene)-dimethyl-ammonium Boron Tetrafluoride was added (32.75 g, 102.0 mmol). The suspension was heated to 60° C. for 1 hr. before the thick suspension was allowed to cool down to RT. The resulting suspension was filtered, washed with chloroform (200 mL) and dried under vacuum overnight to afford the title compound 6a as a light yellow powder (32.5 g, 88%).

Preparation 2b: (6-chlorobenzotriazol-1-yl)-2-amino-6-fluoro-pyrazolo[1,5-a]pyrimidine-3-carboxylate 6b

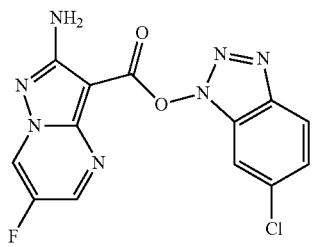

6b

In a 2.5 L three-necked flask equipped with stirrer bar, condenser, nitrogen line and Hanna temperature probe was charged 2-amino-6-fluoro-pyrazolo[1,5-a]pyrimidine-3-carboxylic acid 5 (60 g, 305.9 mmol), chloroform (900.0 mL) and triethylamine (32.44 g, 44.68 mL, 320.6 mmol). [(6-chlorobenzotriazol-1-yl)oxy-(dimethylamino)methylene]-dimethyl-ammonium (Boron Tetrafluoride Ion (1)) (87.00 g, 244.7 mmol) was added portionwise over 5 mins (internal dropped from 22.7 to 21.5° C. on complete addition). Mixture heated at 60° C. (internal temp) for 2 hr., still a cream suspension. Mixture cooled to room temperature then solid collected by filtration, washed well with chloroform (until filtrate runs essentially colourless) and dried by suction to leave product 6b as a cream solid (82.2 g, 77% yield). $^1$H NMR (500 MHz, DMSO-d$_6$) δ 9.55 (dd, 1H), 8.91 (d, 1H), 8.22 (dd, 1H), 8.09 (dd, 1H), 7.57 (dd, 1H) and 6.87 (s, 2H). MS (ES+) 348.1.

In an alternative method, 2-Amino-6-fluoropyrazolo[1,5-c]pyrimidine-3-carboxylic acid 5 (30 g, 153 mmol) was slurried in acetonitrile (540 ml). Triethylamine (22.5 ml, 153 mmol) was added, followed by [(6-chlorobenzotriazol-lyl)oxy-(dimethylamino)methylene]-dimethylammonium tetrafluoroborate (TCTU, 54.4 g, 153 mmol). The mixture was stirred at room temperature for 2 hrs. The product was isolated by filtration—the filter cake was washed with acetonitrile (2×60 ml). The product was obtained as a brown solid (49.3 g, 93%); $^1$H NMR (500 MHz, DMSO-d$_6$) δ 9.55 (dd, 1H), 8.91 (d, 1H), 8.22 (dd, 1H), 8.09 (dd, 1H), 7.57 (dd, 1H) and 6.87 (s, 2H); 19F NMR (500 MHz, DMSO-d6) δ -150.1; MS (ES+) 348.1.

Example 1

Synthesis of 2-amino-6-fluoro-N-(5-fluoro-4-(1-methyl-1H-imidazol-5-yl)pyridin-3-yl)pyrazolo[1,5-a]pyrimidine-3-carboxamide (Compound I-1)

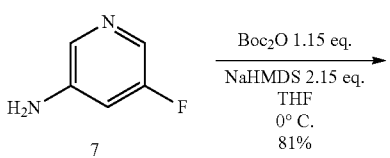

7

Boc$_2$O 1.15 eq.
NaHMDS 2.15 eq.
THF
0° C.
81%

-continued

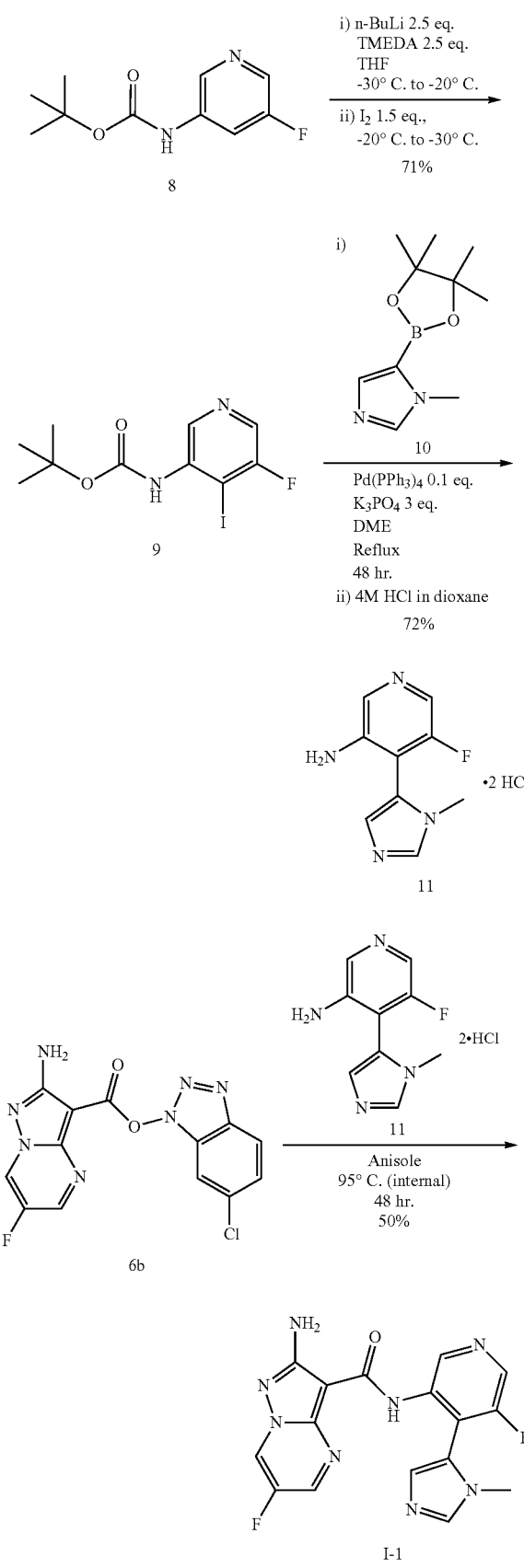

Step 1: tert-butyl (5-fluoropyridin-3-yl)carbamate

In a 50 L jacketed vessel was added THF (2.5 L), 5-fluoropyridin-3-amine 1 (500 g, 4.460 mol) then additional THF (5 L). To this stirred mixture was added a solution of tert-butoxycarbonyl tert-butyl carbonate (1.119 kg, 5.129 mol) in THF (2.5 L), pumped in via a vacuum line. The line was then rinsed with THF (1 L) in to the reaction vessel. The reaction temperature was cooled to 0° C. before NaHMDS (4.794 L of 2 M in THF, 9.589 mol) was added in 12×400 mL portions (approx. 5° C. exotherm after each addition, dosing continued once internal cooled to 0° C.). Addition was completed after 1 hr. The internal temperature was raised to 5° C. and stirred at this temperature for 1 hr. The reaction was carefully quenched by slow addition of a saturated ammonium chloride aqueous solution (1 L) (exothermic). The internal was raised to 10° C. and additional saturated ammonium chloride aqueous solution (3 L) was added. The internal was raised to 25° C. and the reaction mixture was extracted with EtOAc (1×5 L then 1×2.5 L). The combined organic layers were washed with water (1×5.5 L then 1×3 L) then with brine (3 L).

The organic phase was concentrated in vacuo to a total volume of approx. 6 L, dried (MgSO$_4$), filtered through filter paper and concentrated in vacuo (on a rotary evaporator, 40° C. bath temp) until product crystallised out (approx. 2 L of solvent remaining). Heptane (2.5 L) was added and the mixture rotated on a rotary evaporator at 40° C. The solution was concentrated in vacuo (on a rotary evaporator, 40° C. bath temp) to remove more EtOAc until the product crystallised out of solution. The mixture was then left to cool and stand at ambient temperature overnight. The solid was collected by filtration through Whatman No 1 filter paper, washed with heptane until filtrate ran essentially colourless. The solid was dried for approx. 5 hr. to leave crop 1 of product as an off white solid, 382.51 g.

The mother liquor was concentrated slowly in vacuo (on a rotary evaporator, 40° C. bath temp) until a solid crystallised out. The mixture was left to stand at ambient overnight and the solid collected by filtration, washed with heptane and dried by suction to leave crop 2 of product 8 as an off white solid, 203.5 g. The process was repeated on the mother liquor to give crop 3 as an off white solid, 178.7 g. Total yield of product, 764.71 g, 81%. $^1$H NMR (500 MHz, DMSO-d6) δ 9.86 (s, 1H), 8.44 (s, 1H), 8.17 (d, J=2.6 Hz, 1H), 7.83 (d, J=11.6 Hz, 1H), 3.30 (s, 1H). MS (ES+) 213.0.

Step 2: tert-butyl (5-fluoro-4-iodopyridin-3-yl)carbamate

In a 50 L jacket vessel was added THF (2.5 L), tert-butyl N-(5-fluoro-3-pyridyl)carbamate 8 (400 g, 1.885 mol) in THF (2.5 L), additional THF (3 L) and N,N,N',N'-tetramethylethane-1,2-diamine (547.6 g, 711.2 mL, 4.712 mol). The reaction mixture was cooled to −28° C. (internal temperature), then n-BuLi (1.885 L of 2.5 M in hexanes, 4.712 mol) was added via canula at such a rate as to keep internal temperature below −20° C. (i.e., over 2 hr.). On complete addition, the reaction mixture was stirred at between −30 and −20° C. (internal temperature) for a further 50 mins. Solid molecular iodine (765.5 g, 3.016 mol) was slowly added in 12 roughly equal portions over 1 hr. (approx. ⅔° C. delayed exotherm after each portion added) keeping the internal temperature below −20° C. On complete addition of iodine, the reaction mixture was stirred at −30° C. (internal temperature) for a further 45 mins The reaction was then quenched by the slow addition of a saturated ammonium chloride aqueous solution (2 L) (exothermic). Water (2 L) was then added and the reaction mixture warmed to 20° C. (internal temperature) and left to stand overnight. To the reaction mixture was added EtOAc (5 L) and stirring continued for 10 mins. The aqueous phase was removed then a saturated sodium thiosulfate aqueous solution (2 L) was added to the organic phase, stirred vigorously for 10 mins. Additional EtOAc (2.5 L) and water (2 L) was added and stirring continued for 10 mins. The aqueous phase was removed and the organic phase washed further with a saturated sodium thiosulfate aqueous solution (2 L) and water (1×2 L then 1×2.5 L) and then brine (2 L). The organic phase was concentrated in vacuo (rotary evaporator) to such a volume that the product started to crystallise out to give a thick suspension. The mixture was left to stand at room temperature overnight.

The solid was collected by filtration, washed with minimal EtOAc (a few hundred mL) then washed well with heptane, dried by suction for 3 hr. to leave crop 1 of product 9 as a white solid, 311.99 g. The mother liquor was concentrated in vacuo (rotary evaporator) to dryness leaving a dark green solid. (approx 200 g) which was dissolved in EtOAc (750 mL) by heating under reflux. Activated carbon (20 g) was then added and the mixture stirred under reflux for 10 mins. The mixture was filtered through filter paper then concentrated slowly on rotary evaporator until a thick suspension formed. The resulting solid was collected by filtration, washed with minimal EtOAc then heptane, dried by suction then in a vacuum oven at 40° C. for 2 hr., leaving crop 2 as a white solid, 103.9 g. The mother liquor was concentrated again until a thick suspension formed. The solid was collected by filtration, washed with heptane and dried by suction in vacuo (rotary evaporator) then in a vacuum oven at 40° C. for a few hours to leave product crop 3 as a white solid, 39.4 g. Total yield=455.29 g, 71%. $^1$H NMR (500 MHz, DMSO-d6) δ 8.98 (s, 1H), 8.27 (dd, J=1.2, 0.6 Hz, 2H), 1.47 (s, 9H). MS (ES+) 338.9.

Step 3: 5-fluoro-4-(1-methyl-1H-imidazol-S-yl)pyridin-3-amine dihydrochloride

11

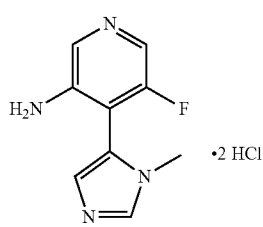

•2 HCl

To a degassed (3× vacuum/nitrogen cycles) mixture of tert-butyl N-(5-fluoro-4-iodo-3-pyridyl)carbamate 9 (190 g, 561.9 mmol), 1-methyl-5-(4,4,5,5-tetramethyl-1,3,2-dioxaborolan-2-yl)imidazole 10 (175.4 g, 842.8 mmol) and potassium phosphate (226.0 g, 1.686 mol) in DME (2.28 L) was added Pd(PPh$_3$)$_4$ (64.93 g, 56.19 mmol). The reaction vessel was again flushed with nitrogen via vacuum/nitrogen cycles (3×). The mixture was heated under reflux and under a nitrogen atmosphere for 48 hr. The mixture was cooled to room temperature then passed through a pad of celite, rinsing through with EtOAc until filtrate almost colourless (approx. 1.5 L). The filtrate was concentrated in vacuo to leave a sticky brown solid, 339.7 g.

The crude product was dissolved in dioxane (950 mL) and methanol (431.1 mL) and the solution cooled on ice bath (internal of 10° C.), HCl (4 M in 1,4-dioxane) (842.8 mL of 4 M, 3.371 mol) was then added in 8 roughly equal portions over 20 mins (approximately 3 to 4° C. exotherm observed on each addition). On complete addition, the mixture was warmed to 40° C. and stirred at this temperature for 3 hr., then left to cool to room temperature overnight with stirring. The solid was collected by filtration, washed with 1,4-dioxane and dried under vacuum for 1 hr. to leave product 11 as a sand/brown solid (107.9 g, 72% yield). $^1$H NMR (500 MHz, Deuterium Oxide) δ 9.09 (s, 1H), 8.24 (s, 1H), 8.15 (br s, 1H), 7.91-7.90 (1H, br s), 7.88 (m, 1H), 3.85 (s, 3H). MS (ES+) 193.1.

Step 4: 2-amino-6-fluoro-N-(5-fluoro-4-(1-methyl-1H-imidazol-5-yl)pyridin-3-yl)pyrazolo[1,5-a]pyrimidine-3-carboxamide (Compound I-1)

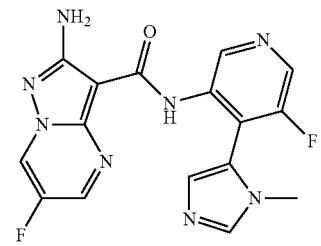

A mixture of 5-fluoro-4-(3-methylimidazol-4-yl)pyridin-3-amine dihydrochloride 11 (8.006 g, 30.2 mmol) and (6-chlorobenzotriazol-1-yl) 2-amino-6-fluoro-pyrazolo[1,5-a]pyrimidine-3-carboxylate 6b (10 g, 28.76 mmol) was suspended in anisole (100 mL). To this suspension was added DIPEA (8.177 g, 11.02 mL, 63.27 mmol) and the mixture was heated at 95° C. (internal temperature) for 44 hr. then allowed to cool to room temperature overnight. The solid was collected by filtration, washed with minimal anisole (approx 20 mL), dried under vacuum for 1 hr., then the solid dried in a vacuum oven at 45° C. (internal temperature) for 2 hr. to leave product as a light yellow solid, 7.8 g. This solid was suspended in water (78 mL) and MeCN (117 mL) and TFA (2.4 g, 1.62 mL, 1 eq.) was added. The reaction mixture was stirred at room temperature for 10 mins. then filtered through filter paper, washed through with small amount of water. The filtrate was basified to pH=8 by addition of 2 M sodium carbonate whilst stirring. The solid was collected by filtration, washed with water then dried under vacuum for 1 hr. The solid was then dried in vacuum oven at 45° C. (internal temperature) overnight leaving product I-1 as a pale yellow solid, 5.29 g. $^1$H NMR (500

MHz, DMSO-d6) δ 9.68 (s, 2H), 9.42 (dd, J=4.8, 2.5 Hz, 1H), 8.46 (s, 1H), 8.31 (d, J=2.5 Hz, 1H), 8.07 (s, 1H), 7.25 (d, J=1.0 Hz, 1H), 6.71 (s, 2H), 3.46 (s, 3H). MS (ES+) 371.0.

Compound Analytical Data

| Cmpd No. | LCMS ES+ | LCMS (Rt min) | HNMR |
|---|---|---|---|
| I-1 | 371.0 | 1.80 | $^1$H NMR (500 MHz, DMSO-d6) δ 9.68 (s, 2H), 09.42 (dd, J = 4.8, 2.5 Hz, 1H), 8.46 (s, 1H), 8.31 (d, J = 2.5 Hz, 1H), 8.07 (s, 1H), 7.25 (d, J = 1.0 Hz, 1H), 6.71 (s, 2H), 3.46 (s, 3H). |

Solid Forms of Compound I-1

Compound I-1 has been prepared in various solid forms, including anhydrous forms. The solid forms of the present invention are useful in the manufacture of medicaments for the treatment of cancer. One embodiment provides use of a solid form described herein for treating cancer. In some embodiments, the cancer is triple negative breast cancer, pancreatic cancer, small cell lung cancer, colorectal cancer, ovarian cancer, or non-small cell lung cancer. Another embodiment provides a pharmaceutical composition comprising a solid form described herein and a pharmaceutically acceptable carrier.

Applicants describe herein a novel solid form of Compound I-1. The name and stoichiometry of the solid form is provided in Table 2 below:

TABLE 2

| Example | Forms | Stoichiometry |
|---|---|---|
| Example 2 | Compound I-1 anhydrous free base | N/A |
| Example 3 | Compound I-1 hydrate | 1:3 |
| Example 4 | Compound I-1 tartaric acid | 1:1 |

Example 2

Compound I-1 (Anhydrous Free Base)

Compound I-1 anhydrous free base can be prepared according to the methods described in Example 1, Step 4.

XRPD of Compound I-1 (Anhydrous Free Base)

The XRPD pattern of compound I-1 anhydrous free base was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were recorded over the range of 3°-39° 2 theta with a step size of 0.013° and a dwell time of 0.5 s per step. FIG. 1a shows the X-ray powder diffractogram of the sample which is characteristic of crystalline drug substance.

Representative XRPD peaks from Compound I-1 anhydrous free base:

| XRPD Peaks | Angle (2-Theta ± 0.2) | Intensity % |
|---|---|---|
| 1 | 8.704 | 35.67 |
| 2* | 9.8727 | 100 |
| 3* | 12.7565 | 34.37 |
| 4* | 15.4224 | 31.96 |
| 5* | 16.9295 | 29.04 |
| 6 | 17.4518 | 6.14 |
| 7 | 18.6901 | 21.74 |
| 8 | 20.5734 | 9.04 |
| 9 | 21.2755 | 9.98 |
| 10 | 21.7139 | 5.54 |
| 11* | 23.0565 | 29.6 |
| 12 | 24.3907 | 14.96 |
| 13 | 25.9089 | 3.38 |
| 14* | 27.8453 | 28.56 |
| 15* | 28.9558 | 17.14 |
| 16* | 30.1162 | 9.76 |
| 17 | 31.7775 | 6.85 |
| 18 | 32.2508 | 2.88 |
| 19 | 33.04 | 3.17 |
| 20 | 33.7887 | 4.71 |
| 21 | 36.5878 | 2.64 |
| 22 | 37.6243 | 0.33 |

Thermo Analysis of Compound I-1 (Anhydrous Free Base)

A thermogravimetric analysis of compound I-1 anhydrous free base was performed to determine the percent weight loss as a function of temperature using the Discovery TGA (TA Instruments Trios). A sample (2.84 mg) was added to a pre-tared aluminum pan and heated from ambient temperature to 400° C. at 10° C./min. The TGA results seen in FIG. 2a show very little observed weight loss prior to melting or thermal degradation. From ambient temperature to 261° C., the weight loss is 0.60%. The onset temperature of melting/degradation is 299° C.

Differential Scanning Calorimetry of Compound I-1 (Anhydrous Free Base)

Differential scanning calorimetry of compound I-1 anhydrous free base was measured using the TA Instrument DSC Q2000. A sample (1.71 mg) was weighed in a pinholed hermetic aluminum pan and heated from ambient temperature to 400° C. at 10° C./min. The DSC results seen in FIG. 3a show a single melting endotherm at 302° C. (onset).

Example 3

Compound I-1 (Hydrate)

Compound I-1 anhydrous free base, prepared according to the methods described in Example 1, Step 4, was slurried in water or organic solvent water mixtures to produce Compound I-1 hydrate.

XRPD of Compound I-1 (hydrate)

The XRPD pattern of Compound I-1 hydrate was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were over the range of 3°-39° 2 theta with a step size of 0.013° and a dwell time of 0.5 s per step. FIG. 1b shows the X-ray powder diffractogram of the sample which is characteristic of crystalline drug substance.

Representative XRPD Peaks from Compound I-1 Hydrate:

| XRPD Peaks | Angle (2-Theta ± 0.2) | Intensity % |
|---|---|---|
| 1 | 7.5 | 100.0 |
| *2 | 27.5 | 52.7 |
| 3 | 6.4 | 43.1 |
| *4 | 20.6 | 23.2 |
| 5 | 27.9 | 22.4 |
| 6 | 18.3 | 16.2 |
| 7 | 17.1 | 15.2 |
| *8 | 9.7 | 13.5 |
| 9 | 30.3 | 13.4 |
| 10 | 11.8 | 12.8 |
| 11 | 28.5 | 12.8 |
| 12 | 15.6 | 12.7 |
| 13 | 16.7 | 11.6 |
| 14 | 18.7 | 10.8 |
| 15 | 22.8 | 10.3 |

Thermo Analysis of Compound I-1 (Hydrate)

A thermal gravimetric analysis (TGA) of Compound I-1 hydrate was performed to determine the percent weight loss as a function of temperature using the Discovery TGA (TA Instruments Trios). A sample (4.74 mg) was added to a pre-tared aluminum pan and heated from ambient temperature to 400° C. at 10° C./min. The TGA results seen in FIG. 2b show a large weight loss of 12.6% below 100° C. This weight loss corresponds to approximately 3 molar equivalents of water. The subsequent weight loss above 250° C. is a result of melting and degradation.

Differential Scanning Calorimetry of Compound I-1 (Hydrate)

Differential scanning calorimetry (DSC) of Compound I-1 hydrate was measured using the TA Instrument DSC Q2000. A sample (2.78 mg) was weighed in a pinholed aluminum hermetic pan and heated from ambient temperature to 370° C. at 10° C./min. The DSC results seen in FIG. 3b show a broad desolvation endotherm below 100° C. followed by a exotherm recrystallization to Compound I-1 anhydrous free base between 100-150° C. The endotherm peak between 300-305° C. indicates the melting of Compound I-1 anhydrous free base.

Example 4

Compound I-1 (Tartaric Acid)

Compound I-1 anhydrous free base, prepared according to the methods described in Example 1, Step 4, was slurried with tartaric acid and ethanol to produce Compound I-1 tartaric acid.

XRPD of Compound I-1 (Tartaric Acid)

The XRPD pattern of Compound I-1 tartaric acid form was recorded at room temperature in reflection mode using a PANalytical diffractometer equipped with an Empyrean tube source and a PIXcel 1D detector (PANalytical, The Netherlands). The X-ray generator was operating at a voltage of 45 kV and a current of 40 mA. The powder sample was placed in a silicon holder. The data were over the range of 4.5°-39° 2 theta with a step size of 0.013° and a dwell time of 299.6 s per step. FIG. 1c shows the X-ray powder diffractogram of the sample which is characteristic of crystalline drug substance.

Representative XRPD peaks from Compound I-1 tartaric acid:

| XRPD Peaks | Angle (2-Theta ± 0.2) | Intensity % |
|---|---|---|
| *1 | 7.1 | 100.0 |
| *2 | 18.3 | 36.7 |
| 3 | 19.2 | 36.2 |
| *4 | 13.2 | 29.2 |
| 5 | 28.0 | 25.8 |
| 6 | 24.8 | 24.2 |
| 7 | 20.3 | 20.3 |
| 8 | 22.2 | 16.9 |
| 9 | 28.9 | 16.4 |
| 10 | 23.7 | 15.7 |
| 11 | 28.4 | 14.3 |
| 12 | 10.6 | 14.1 |
| 13 | 10.3 | 12.0 |

Thermo Analysis of Compound I-1 (Tartaric Acid)

A thermal gravimetric analysis (TGA) of Compound I-1 tartaric acid form was performed to determine the percent weight loss as a function of temperature using the Discovery TGA (TA Instruments Trios). A sample (3.35 mg) was added to a pre-tared aluminum pan and heated from ambient temperature to 330° C. at 10° C./min. The TGA results seen in FIG. 2c show three step weight losses of 12.4%, 12.6%, and 8.5% between 150-330° C.

Differential Scanning Calorimetry of Compound I-1 (Tartaric Acid)

Differential scanning calorimetry (DSC) of Compound I-1 tartaric acid was measured using the TA Instrument DSC Q2000. A sample (1.08 mg) was weighed in a pinholed aluminum hermetic pan and heated from ambient temperature to 350° C. at 10° C./min. The DSC results seen in FIG. 3c show the first 2 exotherm peaks between 200-275° C. corresponding to the first 2 step weight losses in TGA, and the last endoterm peak above 275° C. corresponding to the last step weight loss in TGA.

Example 5

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 μM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry,* 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 6

ATR Inhibition Assay

Compounds can be screened for their ability to inhibit ATR kinase using a radioactive-phosphate incorporation assay. Assays are carried out in a mixture of 50 mM Tris/HCl (pH 7.5), 10 mM $MgCl_2$ and 1 mM DTT. Final substrate concentrations are 10 µM [γ-33P]ATP (3 mCi 33P ATP/mmol ATP, Perkin Elmer) and 800 µM target peptide (ASELPASQPQPFSAKKK).

Assays are carried out at 25° C. in the presence of 5 nM full-length ATR. An assay stock buffer solution is prepared containing all of the reagents listed above, with the exception of ATP and the test compound of interest. 13.5 µL of the stock solution is placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate is pre-incubated for 10 minutes at 25° C. and the reaction initiated by addition of 15 µL [γ-33P]ATP (final concentration 10 µM).

The reaction is stopped after 24 hours by the addition of 300 µL 0.1M phosphoric acid containing 2 mM ATP. A multiscreen phosphocellulose filter 96-well plate (Millipore, Cat no. MAPHN0B50) is pretreated with 100 µL 0.2M phosphoric acid prior to the addition of 45 µL of the stopped assay mixture. The plate is washed with 5×200 µL 0.2M phosphoric acid. After drying, 100 µL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

In general, the compounds of the present invention are effective for inhibiting ATR. Compound I-1 inhibits ATR at Ki values below 1 µM.

Example 7

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

In general, the compounds of the present invention are effective for sensitizing cancer cells to Cisplatin. Compound I-1 have Cisplatin sensitization values of <0.2 µM.

Example 8

Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Example 9

ATR-Complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM MgCl$_2$ and 1 mM DTT. Final substrate concentrations were 10 μM [g-33P]ATP (3.5 μCi 33P ATP/nmol ATP, Perkin Elmer, Massachusetts, USA) and 800 μM target peptide (ASELPASQPQPFSAKKK, Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1(A891-S1105). An enzyme stock buffer solution was prepared containing all of the reagents listed above, with the exception of target peptide, ATP and the test compound of interest. This enzyme stock was pre-incubated for 30 minutes at 25° C. 8.5 μL of the enzyme stock solution was placed in a 96-well plate followed by addition of 5 μl of target peptide and 2 μL of DMSO stock containing serial dilutions of the test compound (typically starting from a final concentration of 1.5 μM with 2.5-fold serial dilutions) in duplicate (final DMSO concentration 7%). The plate was pre-incubated for 10 minutes at 25° C. and the reaction initiated by addition of 15 μL [g-33P]ATP (final concentration 10 μM).

The reaction was stopped after 20 hours by the addition of 30 μL 0.3 M phosphoric acid containing 2 mM ATP. A phosphocellulose filter 96-well plate (Multiscreen HTS MAPHN0B50, Merck-Millipore, Massachusetts, USA) was pretreated with 100 μL 0.1 M phosphoric acid prior to the addition of 45 μL of the stopped assay mixture. The plate was washed with 5×200 μL 0.1 M phosphoric acid. After drying, 50 μL Optiphase 'SuperMix' liquid scintillation cocktail (Perkin Elmer, Massachusetts, USA) was added to the well prior to scintillation counting (Wallac 1450 Microbeta Liquid Scintillation Counter, Perkin Elmer, Massachusetts, USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A solid form of Compound I-1:

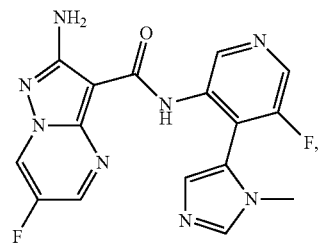

I-1 wherein the form is a crystalline form of the anhydrous free base of Compound I-1 characterized by one or more peaks expressed in 2-theta±0.2 at about 9.9, 12.8, 15.4, 17.0, 23.1, 27.8, 29.0, and 30.1 degrees in an X-Ray powder diffraction pattern obtained using Cu K alpha radiation.

2. A solid form of Compound I-1:

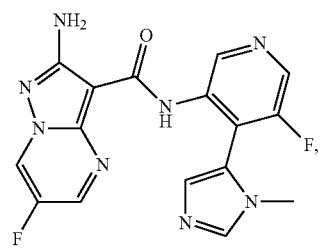

I-1 wherein the form is a crystalline form of Compound I-1 hydrate having a Compound I-1 to water ratio of 1:3.

3. A solid form of Compound I-1:

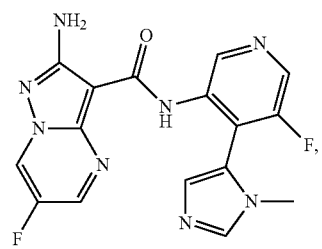

I-1 wherein the form is a crystalline form of Compound I-1 tartaric acid having a Compound I-1 to tartaric acid ratio of 1:1.

* * * * *